US007311752B2

(12) United States Patent
Tepper et al.

(10) Patent No.: US 7,311,752 B2
(45) Date of Patent: Dec. 25, 2007

(54) ELECTROSTATIC AIR FILTER

(75) Inventors: Frederick Tepper, Sanford, FL (US); Leonid A. Kaledin, Port Orange, FL (US)

(73) Assignee: Argonide Corporation, Sanford, FL (US)

( * ) Notice: Subject to any disclaimer, the term of this patent is extended or adjusted under 35 U.S.C. 154(b) by 0 days.

(21) Appl. No.: 11/531,107

(22) Filed: Sep. 12, 2006

(65) Prior Publication Data

US 2007/0056256 A1 Mar. 15, 2007

Related U.S. Application Data

(60) Provisional application No. 60/716,218, filed on Sep. 12, 2005.

(51) Int. Cl.
*C02F 1/00* (2006.01)

(52) U.S. Cl. ..................... 55/528; 55/527; 55/DIG. 39; 95/273; 95/285; 210/660; 210/500.1; 210/505; 210/510.1; 423/627; 423/629; 436/177

(58) Field of Classification Search .................. 55/527, 55/528, 523, DIG. 39; 95/273, 385, 285; 210/500.1, 505, 510.1, 660; 423/627, 629; 436/177, 178
See application file for complete search history.

(56) References Cited

U.S. PATENT DOCUMENTS

| | | | | |
|---|---|---|---|---|
| 2,773,601 | A | 12/1956 | Keller et al. | |
| 2,915,475 | A * | 12/1959 | Bugosh | 516/94 |
| 3,234,075 | A * | 2/1966 | Braitberg | 162/161 |
| 3,852,202 | A * | 12/1974 | Wells et al. | 507/205 |
| 4,059,119 | A | 11/1977 | Grossman | |
| 4,149,549 | A | 4/1979 | Grossman | |
| 4,153,661 | A * | 5/1979 | Ree et al. | 264/120 |
| 4,242,226 | A | 12/1980 | Siren | |
| 4,305,782 | A * | 12/1981 | Ostreicher et al. | 162/181.6 |
| 4,395,332 | A | 7/1983 | Klein | |
| 4,433,697 | A | 2/1984 | Cline et al. | |
| 4,455,187 | A | 6/1984 | von Blucher et al. | |

(Continued)

FOREIGN PATENT DOCUMENTS

EP 1219335 7/2002

OTHER PUBLICATIONS

Wilkie, A.E. et al., Multi-Component Fiber Technology for Medical and Other Filtration Applications, 1st Inter. Conf. on Med. Filtration, DE Oct. 9, 2002.

(Continued)

*Primary Examiner*—Duane Smith
*Assistant Examiner*—Minh-Chau T. Pham
(74) *Attorney, Agent, or Firm*—Thomas C. Wettach, Esq.; Alicia M. Passerin, Esq.; Cohen & Grigsby, P.C.

(57) ABSTRACT

The invention is a filter for gaseous media in which nano alumina fibers and second fibers are arranged in a matrix to create asymmetrical pores. The filter is a high efficiency, high capacity particulate filter that intercepts pathogens and other particulate matter from gaseous media, including vapor-suspended particles. The new filter has an improved retention of water-aerosolized particles as compared to conventional HEPA filters and may be used as a pre-filter that extends the life of HEPA filters by about five to ten times. The invention is also a method of manufacturing and using the filter.

44 Claims, 14 Drawing Sheets

U.S. PATENT DOCUMENTS

| | | | |
|---|---|---|---|
| 4,500,647 A * | 2/1985 | Solomon | 502/101 |
| 4,510,193 A | 4/1985 | Blucher et al. | |
| 4,536,440 A | 8/1985 | Berg | |
| 4,555,347 A | 11/1985 | O'Dowd et al. | |
| 4,606,823 A | 8/1986 | Lucas, III | |
| 4,664,683 A | 5/1987 | Degen et al. | |
| 4,677,019 A | 6/1987 | von Blucher | |
| 4,807,619 A | 2/1989 | Dyrud et al. | |
| 4,824,451 A | 4/1989 | Vogt et al. | |
| 5,109,311 A | 4/1992 | Hanazono et al. | |
| 5,126,044 A | 6/1992 | Magnusson et al. | |
| 5,147,722 A | 9/1992 | Koslow | |
| 5,187,092 A | 2/1993 | Koslow | |
| 5,225,078 A | 7/1993 | Polasky et al. | |
| 5,307,796 A | 5/1994 | Kronzer et al. | |
| 5,350,443 A | 9/1994 | von Blucher et al. | |
| 5,366,636 A | 11/1994 | Marchin et al. | |
| 5,486,292 A | 1/1996 | Bair et al. | |
| 5,562,824 A | 10/1996 | Magnusson | |
| 5,744,236 A | 4/1998 | Rohrbach et al. | |
| 5,759,394 A | 6/1998 | Rohrbach et al. | |
| 5,804,295 A | 9/1998 | Braun et al. | |
| 5,865,968 A | 2/1999 | Denton et al. | |
| 6,010,606 A | 1/2000 | Denton et al. | |
| 6,077,588 A | 6/2000 | Koslow et al. | |
| 6,235,388 B1 | 5/2001 | Yamamoto et al. | |
| 6,290,848 B1 | 9/2001 | Tanner et al. | |
| 6,321,915 B1 | 11/2001 | Wilson et al. | |
| 6,355,330 B1 | 3/2002 | Koslow et al. | |
| 6,402,819 B1 | 6/2002 | DeRuiter et al. | |
| 6,464,757 B2 | 10/2002 | Zhang et al. | |
| 6,514,413 B2 | 2/2003 | Pimenov et al. | |
| 6,524,477 B1 | 2/2003 | Hughes | |
| 6,550,622 B2 | 4/2003 | Koslow | |
| 6,630,016 B2 | 10/2003 | Koslow | |
| 6,716,218 B2 | 4/2004 | Holmes et al. | |
| 6,716,525 B1 | 4/2004 | Yadav et al. | |
| 6,797,167 B2 | 9/2004 | Koslow | |
| 6,830,822 B2 | 12/2004 | Yadav | |
| 6,838,005 B2 * | 1/2005 | Tepper et al. | 210/660 |
| 6,849,109 B2 | 2/2005 | Yadav et al. | |
| 6,872,431 B2 * | 3/2005 | Kahlbaugh et al. | 428/36.1 |
| 6,913,154 B2 | 7/2005 | Koslow | |
| 6,953,604 B2 | 10/2005 | Koslow | |
| 6,955,708 B1 | 10/2005 | Julos et al. | |
| 6,959,820 B2 | 11/2005 | Koslow | |
| 2003/0127393 A1 * | 7/2003 | Tepper et al. | 210/656 |
| 2005/0011827 A1 * | 1/2005 | Koslow | 210/503 |
| 2005/0029198 A1 | 2/2005 | Tepper et al. | |
| 2006/0123991 A1 | 6/2006 | Braeunling et al. | |
| 2006/0163174 A1 | 7/2006 | Namespera et al. | |
| 2006/0169144 A1 | 8/2006 | Forslund | |
| 2006/0225574 A1 | 10/2006 | Braeunling et al. | |

OTHER PUBLICATIONS

Raynor, P.C. et al., The Long-Term Performance of Electrically Charged Filters in a Ventilation System, J. of Occ. and Envir. Hygiene, vol. 1(7): 463-471, Jul. 2004.

Martin, S.M. et al., Electrostatic Respirator Filter Media: Filter Efficiency and Most Penetrating Particle Size Effects, Appl. Occ. & Envir. Hygiene vol. 15(8): 609-17, 2000.

Moyer, E.S. et al., Electrostatic N-95 Respirator Filter Media Efficiency Degradation Resulting from Intermittent NaCl Aerosol Expos., Appl. Occ. & Envir. Hyg. 15(8): 600-8.

Brown, R.C. et al., Effect of Industrial Aerosols on the Performance of Electrically Charged Filter Material, Hyg. vol. 32(3): 271-94, 1988.

Henderson, D.W. et al., An Appartus for the Study of Airborne Infection, J. Hyg. Camb. vol. 50, p. 53-67, 1952.

Johnson, P.R., Whadaya Mean?, Filtration News vol. 20(5): 10-11, 2002.

Blackford, D.B et al., Alteration in the Performance of Electrostatic Filters Caused by Exposure to Aerosols, 4th World Filtration Congress, 7.27-7.33.

Tien, Chi, Adsorption Calculations and Modeling, 1994 Butterworth-Heinemann (TOC provided).

\* cited by examiner

ELECTROSTATIC AIR FILTER

CROSS-REFERENCE TO RELATED APPLICATION

This application claims priority to U.S. Provisional Patent Application No. 60/716,218 entitled "Electrostatic Air Filter," filed on Sep. 12, 2005.

GOVERNMENT INTERESTS

The subject invention was made with support under a research project supported by the United States Air Force, Contract # FA8650-05-M-5822, May 2, 2005, to Nov. 15, 2005. Accordingly, the government has certain rights in this invention.

FIELD OF THE INVENTION

The present invention relates to nano fibers, and particularly to the use of nano alumina fibers in mixtures used in air and gas filters.

BACKGROUND

Indoor and outdoor air quality has become an important occupational health, political, scientific, and environmental topic over the past two decades. Air and gas streams carry various particles therein. Removal of these particles improves air quality and reduces the risk of infection or other ailments that result from air pollution caused by these airborne particles. Good air quality is particularly important for those who suffer from respiratory ailments such as asthma.

One of the major sources of infection is from airborne microbes when soil, water, dust, and decaying organic matter are disturbed. They can be carried indoors by any number of vehicles, including people, air currents, water, equipment, or construction materials. Once indoors, the attendant microorganisms can proliferate in a variety of indoor ecological niches and, if subsequently disbursed into the air, can serve as a source for airborne infections.

Additionally, pathogens such as the influenza virus, rhinoviruses, adenoviruses, respiratory syncytial virus (RSV), tuberculosis, and the measles virus can be spread by aerosolized oral and nasal secretions. Often, these pathogens are contained in either droplets or droplet nuclei ranging in size from 1 µm-5 µm. These droplets remain suspended indefinitely in air and can be transported over long distances. The dispersal of virus into air can be exacerbated by coughing and sneezing that spreads a cloud of pathogens into the air.

Furthermore, many industries generate significant amounts of liquid aerosols that contribute to indoor air pollution. Examples of these liquid aerosols are: metal working fluid mists generated by mechanical industries; paint mists generated in the automobile industry; pesticides used in the agricultural industry; ink mists generated in the graphical industry; and acid mists generated in the chemical industry. Not only do these liquid aerosols have adverse affects on workers' health, but environmental standards are increasingly more stringent and require more efficient filters for reducing air pollution and improving air quality.

Airborne transmission of particulate matter, including those in liquid aerosols, is also especially problematic in healthcare facilities, contributing to the approximately 103, 000 deaths annually caused by infection in U.S. hospitals. Susceptibility to these airborne pathogens is greatest among immune deficient patients such as the elderly, burn patients, and those receiving implants or chemotherapy treatments. Surgeons and other healthcare professionals are also exposed to pathogens carried by liquid aerosols into the operating room, for example, and run the risk of these pathogens reaching the nasal mucosa. For example, the air can be polluted by viruses and bacteria, including human papilloma virus (HPV), HIV, and *Staphylococcus*, that are released in the laser plume of surgical equipment used to section bone. In another example, *legionella* spp. are commonly found in warm water distribution systems and can be disseminated into the air space above it. Locally produced distilled water provides an environment in which *legionella* can multiply. In several hospital outbreaks, healthcare providers have determined that patients were infected by exposure to contaminated aerosols generated by cooling towers, showers, faucets, respiratory therapy equipment, and room air humidifiers.

Air filters are one tool that consumers, industry, and healthcare facilities alike rely on to improve air quality. For example, many consumers use home air purifiers or filters in their vacuum cleaners to improve air quality in the home. Healthcare providers and those working in industry often rely on face masks to protect them from airborne particulate matter and pathogens. A commonly used type of air and gas filter is one that has a HEPA (High Efficiency Particle Air) filtration media. HEPA filtration media are capable of retaining >99.97% of 0.3 µm particles and consist of a non-woven sheet composed of glass and/or polymeric fibers ranging in diameter from about 0.5 to about 10 µm. These filters are used primarily in collective protection (room) filter systems, although they may also be used in respirators. Ultra Low Penetration Air (ULPA) filtration media are capable of retaining 99.99% of a specified particle size at a specified media velocity. SULPA (Super ULPA) filters are available for use in environments where maximum cleanliness is required. These filters have an efficiency of 99.9999% on the same basis as ULPA filters.

Despite HEPA air filter's exceptional retention rate for particulate matter in air or gas streams, these conventional HEPA filter media are susceptible to penetration by liquids, thereby limiting their effectiveness for capturing or retaining pathogens from liquid aerosols. Liquid aerosol clogging occurs when liquid particles, particularly water aerosols, collect on the fibers and create a thin film that covers each fiber. When this film joins two or more fibers together, pools and bridges form that restrict flow and rapidly increase the pressure drop, thereby causing a resultant decrease in filter efficiency. As such, those relying on filters to protect them from pathogens and other particles present in liquid aerosols remain susceptible to infection because currently available filtration media function less efficiently under such circumstances.

The use of nano fibers distributed over microglass fibers for filtering sub-micron particles from water is known in the art. However, such filters have high pressure drops that negate their effectiveness as an air or gas filter. For example U.S. Pat. No. 6,838,005 describes a nano alumina filter that is effective for filtering virus from water. Until the present invention, it was generally believed that any attempts to lower the pressure drop in nano alumina filters would require pore sizes that were far too large to effectively filter fine particles from the air. Further, it was presumed that bulk water was necessary to effect the nano alumina's zeta potential and therefore its electrostatic benefits, thereby negating its use as an air filter.

Additionally, the energy consumed in overcoming the pressure drop in a filter is often more than the cost of the filter itself. With a HEPA filter system, the energy consumed can be four to five times the initial cost of the filter. Therefore, a filter that reduces the pressure drop over the whole life cycle of the filter would provide significant savings. Furthermore, in instances where the filter material is used in a medical application or where it might contain bacteria, then the waste disposal costs escalate rapidly because the filter material is considered to be biohazardous waste. As such, a longer life filter minimizes the frequency of disposing of biohazardous filters and therefore reduces costs.

Given this, there is a need among consumers, healthcare facilities, and other industries for a cost-effective high efficiency filter that retains particles at a level that is at least as high as HEPA filters, but that is also able to intercept water-aerosolized bacteria and that would be superior to conventional HEPA filters for air purification. Such filters would be particularly beneficial for air purification in environments such as hospitals and health care facilities, in pharmaceutical settings such as during drug preparation, in biological safety hoods, and for generally removing mold, fungus and mildew spores from the air and liquid aerosols. Such filters would also be beneficial in collective protection and in personal respirators, such as for protecting military personnel from biological attack, for protecting the homeland from a terrorist attack that utilizes bacteria or viruses, and/or during clean-up of attacked sites such as the World Trade Center.

SUMMARY OF THE INVENTION

The present invention is a new particulate filter or filter media for gaseous media that satisfies the need for a high efficiency and high capacity particulate filter that intercepts pathogens and other particulate matter from air or gas streams, including liquid aerosolized particulate matter while also having a low pressure drop. Accordingly, it is an object in an embodiment of the present invention to provide a filter that has a filtration efficiency that is at least as high as conventional HEPA filters and that is resistant to liquid aerosol clogging.

It is yet another object in an example of an embodiment of the invention to provide a filter media that filters liquid aerosolized bacteria and viruses.

It is a further object in an example of an embodiment of the present invention to produce an air filter that has a high porosity and is therefore more tolerant of adsorbing aqueous mists than conventional filter material.

It is still a further object in an example of an embodiment of the invention to provide a filter media that has a filtration efficiency that is at least as high as conventional ULPA or Super ULPA filters.

It is still a further object in an example of an embodiment of the invention to provide a filter media that has a pressure drop that is lower than that which occurs in conventional filters.

It is still a further object in an example of an embodiment of the invention to provide a filter media that has a larger pore size and higher porosity than that in HEPA filters, therefore providing for a higher capacity for water droplets before flooding.

It is still a further object in an example of an embodiment of the invention to provide a filter media that is energy-efficient.

It is yet another object in an example of an embodiment of the present invention to provide a filter media that has an extended filter life compared to conventional filters.

It is yet another object in an example of an embodiment of the present invention to provide a filter media that has low maintenance costs.

It is still a further object in an example of an embodiment of the present invention to provide a filter media that filters hazardous waste materials and that has minimal costs associated therewith.

It is yet another object in an example of an embodiment of the present invention to provide a filter media that is strong enough to be pleated.

It is another object in an example of an embodiment of the present invention to provide a method of manufacture of a filter or filter media that filters gaseous media at a filtration efficiency that is at least as high as conventional HEPA filters and that is resistant to liquid aerosol clogging.

It is yet another object in an example of an embodiment of the present invention to provide a method of using a filter or filter media to remove particulates and aerosols from gaseous media.

Generally, the present invention is a filter or filter media for gases or mixtures of gases. The filter media comprises nano alumina fibers that adsorb particles from the air or gas stream and a plurality of second fibers arranged in a matrix with the nano alumina fibers to create asymmetrical pores. In an example, the second fibers are comprised of fibers whose minor dimension is larger than the minor (smallest) dimension of the nano alumina fibers by about one order of magnitude. The second fibers are included with the nano alumina fibers in order to provide a scaffolding for creating pores or large interfiber spaces into or onto which nano alumina fibers are dispersed. In examples, the asymmetric pores have an average pore size of greater than about 5 μm. In a preferred example, the average pore size is greater than about 10 μm. In a more preferred example, the average pore size is greater than about 20 μm. In an example, the media removes particulate matter from an air or gas stream. In another example, the media removes liquid aerosols from the air or gas stream.

Coarse fibers provide or form larger pores into or onto which nano alumina fibers are dispersed. However, coarse fibers have less surface area per unit volume or mass, and therefore the amount of nano alumina dispersed thereon or in the pores is significantly reduced. Therefore, in another embodiment, second fibers are comprised of a combination of coarse and fine fibers. The inclusion of fine fibers provides additional surface area so that more nano alumina fibers can be loaded into or onto the media.

In another embodiment, the invention is directed to a method of manufacturing the filter media. The method of manufacture comprises the steps of: forming nano alumina fibers in the presence of a plurality of second fibers. The second fibers are arranged to form a plurality of asymmetrical pores. In an example, the nano alumina filter media is formed into a homogenous filter media as a typical depth filter. In another example, the nano alumina filter media is pleated. In yet another example, the nano alumina filter media is formed into more than one layer.

In another embodiment, the invention is directed to a method of using the nano alumina filter media to remove particulate matter suspended in air or gas streams. In an example, the filter media is used to remove liquid, and particularly water, aerosolized particulate matter suspended in vapor The method of use comprises the steps of: passing a gaseous media through a filter media comprised of a plurality of nano alumina fibers blended with a plurality of second fibers arranged in a matrix to create a plurality of asymmetrical pores therebetween; and removing particulate matter from the gaseous medium.

Those and other details, objects and advantages of the present invention will become better understood or apparent from the following descriptions, examples, and figures showing embodiments thereof.

DETAILED DESCRIPTION

Figure 1:
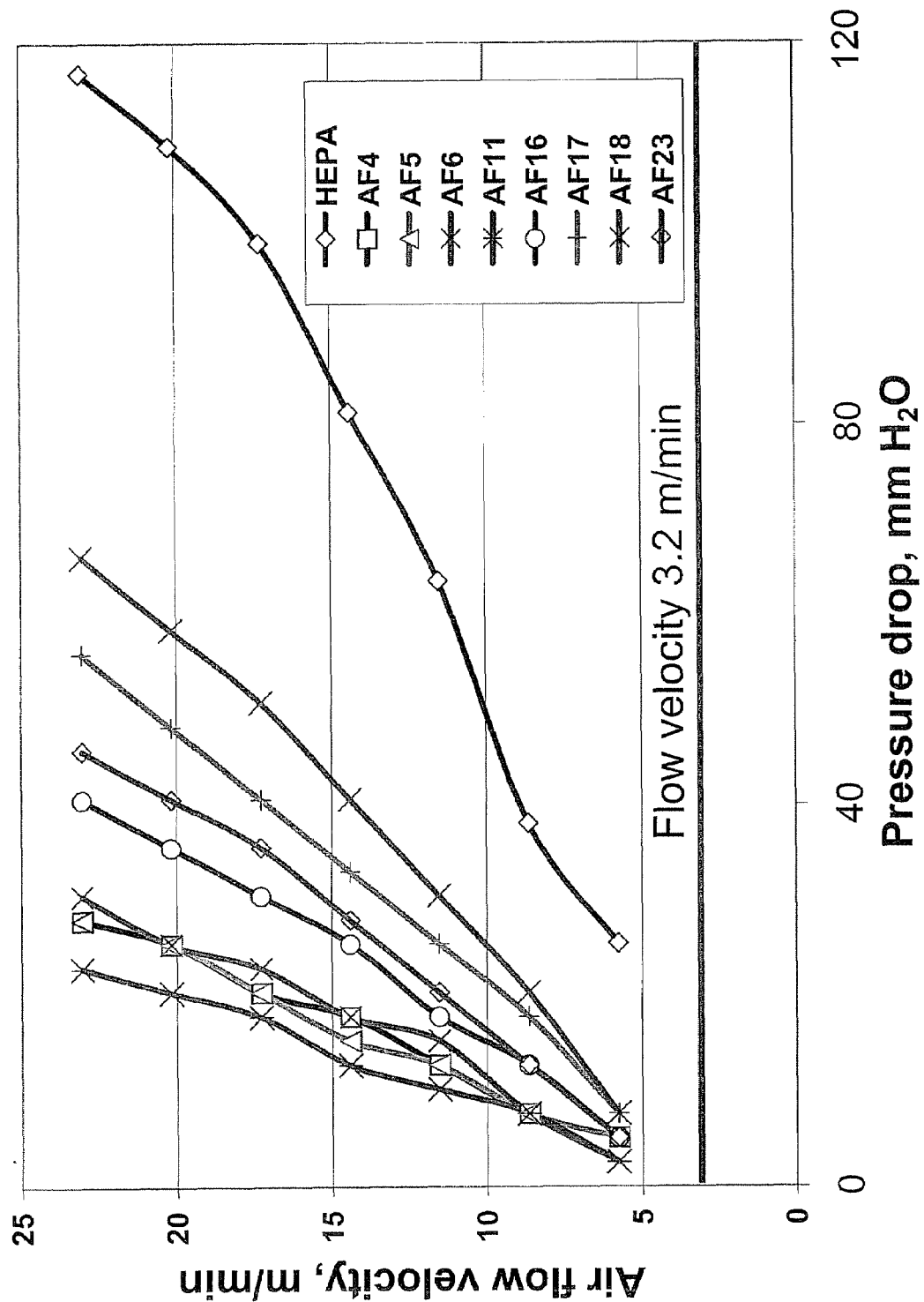
FIG. 1 is a graphical depiction of air flow velocities through the claimed nano alumina filters and a HEPA filter as a function of pressure drop across the filters.

In order to properly understand the disclosure of the claimed invention, certain terms used herein are described in the following paragraph. While the inventors describe the following terms, the inventors in no way intend to disclaim the ordinary and accustomed meanings of these terms.

The term electrostatic as used herein is defined as of or relating to electric charges.

The term aspect ratio as used herein is defined as the ratio of the longitudinal length of a fiber to the cross-sectional diameter of the fiber.

The term nano alumina as used herein is defined as fibers having an aspect ratio in excess of about 5, where the smallest dimension is less than about 50 nm. The cross section of the fiber may be either circular (cylindrical fiber) or rectangular (platelet) in shape. The fibers are comprised of alumina, with various contents of combined water to result in compositions principally of AlOOH with various amounts of $Al(OH)_3$, with possible impurities of gamma and alpha alumina.

The term "Lyocell" as used herein refers to a fibrillated cellulose fiber precipitated from an organic solution in which no substitution of hydroxyl groups takes place and no chemical intermediates are formed (Courtaulds, Ltd.).

The term "High Efficiency Particle Air" (HEPA) refers to a grade of filter media that is capable of retaining >99.97% of 0.3 µm particles.

The term "Ultra Low Penetration Air" (ULPA) refers to a grade of filter media that is capable of retaining >99.99% of a specified particle size at a specified medium velocity.

The term "Super ULPA" refers to a grade of filter media that is capable of retaining >99.9999% of a specified particle size at a specified medium velocity.

The present invention provides a filter media for removing particles, including liquid and particularly water aerosolized particles, from an air or gas stream or other gaseous medium that is passed through the media in order to reduce air pollution and improve air quality. In examples, the particles are pathogens such as bacteria, viruses, mold, fungi, mildew, organic matter, inorganic matter, microorganisms, carbonaceous particles, metal working fluid mists, paint mists, pesticides, ink mists, or acid mists. In examples, the air or gas stream has liquid aerosolized particles such as water aerosolized particles. In an example, the filter media is a non-woven, electrostatic media. The filter media comprises nano alumina fibers mixed with second fibers. In an example, the nano alumina are non-spherical. The second fibers are arranged in a matrix to create asymmetrical pores. In an example, fine metallic aluminum powder is reacted with the second fibers to form the electrostatic media. The reaction is carried out by adding ammonia to the aluminum and second fiber mixture. The mixture is heated to the boiling point of water. In another example, aluminum trihydroxide is heated under conditions of high temperature and pressure in the presence of the second fibers to form the electrostatic media. The reaction is carried out at about 175° C. and approximately 5 bar for about thirty minutes.

Second fibers may be any fiber that is strong enough to tolerate pleating, including microglass, cellulose, or fibrillated cellulose. In an example, second fibers have a minor dimension that is larger than the minor dimension of the nano alumina fibers by at least about one order of magnitude. In examples, average pore sizes range from about 4 to about 48 µm. Preferably, average pore size is greater than about 10 µm. More preferably, average pore size is greater than about 20 µm. In general, pore size is related to the diameter of second fibers. Therefore, a plurality of second fibers having a small diameter will create a plurality of asymmetrical pores having small pore sizes, while a plurality of second fibers having a larger diameter will create a plurality of asymmetrical pores having comparatively larger pore sizes. See, e.g., Table 1 and FIG. 13. However, as the diameter of the second fiber increases, the surface area to unit volume ratio decreases and as a result fewer nano alumina fibers are dispersed on the second fibers and/or in the pores. Therefore, in a preferred example, the plurality of second fibers is comprised of a combination of a plurality of coarse and a plurality of fine fibers. Fine fibers may all have substantially similar average diameters, or some fine fibers may have different diameters. The inclusion of fine fibers results in a corresponding reduction in pore size. See, e.g., Table 1 and FIG. 13.

The pore sizes determine the pressure drop across the filter media. In a preferred example, the pressure drop is less than about 35 mm $H_2O$ for a final composite filter or filtration unit at a flow velocity of about 3.2 m/min.

In an example, the claimed filter media further comprises a granular sorbent, preferably a colloidal particle that is added to the filter media. To adsorb volatile organics, nerve agents, or mustard gas, granular activated carbon is added as a fine powder (for example about 3 to 5 μm carbon dust) to provide more rapid adsorption than typical larger granular carbons. In another example, granular iron oxide or hydroxide, preferably of colloidal size, can be added to improve the adsorption of dissolved arsenites and arsenates. A granular material such as fumed silica or iron oxide could also be added to improve on the nano alumina content, further increasing the performance of the filter media for general particulate removal applications.

In an example, the claimed filter media further comprises a binder. The binder may have a fiber shape (Invista T104) or may be a resin such as Rohm or Haas Rhoplex HA-16. Inclusion of binder increases strength and/or pleatability of the fiber media.

In an example, the filter media may further comprise an antimicrobial agent that is mixed with the plurality of nano alumina and second fibers. In manufacture, after the slurry is made and before the mixture is filtered onto a screen, the antimicrobial agent is added and adsorbed to the nano alumina fibers in order to make it available as an antimicrobial agent. In an example, the antimicrobial agent is silver. In other examples, ions such as copper and zinc work either synergistically with silver as an antimicrobial agent. In yet another example, ions such as copper and zinc work alone as an antimicrobial agent.

In an example of the present invention, the filter media is electrostatically charged, such that the nano alumina fibers capture particles such as pathogens and other matter. In an example, the filter media is a homogenous non-woven filter. In other examples, the filter media is pleated to increase the surface area of the filter media by about 7-10 times compared to non-pleated filter media. The increased filter media surface area reduces the flow speed through the filter, thereby substantially enhancing filtration efficiency. The increased surface area also provides greater capacity for filtering particles, thereby increasing the time it takes for the pressure drop to build up.

In another example, the filter media is layered or stacked, for example by rolling the media around a perforated post, in order to enhance retention. The need for layering may occur where pore sizes are greater than about 25 μm.

In an example, the filter media is pretreated or preconditioned by flowing a plurality of particles therethrough. Particles may have diameters ranging from about 0.3 to about 1.5 μm. Inclusion of these particles blocks at least some of the largest pores of the plurality of asymmetrical pores in order to reduce initial leakage through the filter media. Additionally, preconditioning helps to create or produce HEPA or ULPA capability throughout the use of the filter. In an example, the plurality of particles is a plurality of latex spheres, although the plurality of particles may be made of any substance that is able to block at least some of the largest pores.

In an example, the claimed nano alumina filter media has a retention efficiency that is at least as good as HEPA. In another example, the claimed filter media has a retention efficiency that is at least as good as ULPA.

In another embodiment, the claimed invention is a method of manufacturing the nano alumina filter for gaseous media. The method of manufacture comprises the steps of forming nano alumina fibers in the presence of a plurality of second fibers. The second fibers are arranged to form a plurality of asymmetrical pores. In an example, the nano alumina filter media is formed into a homogenous single layer. In another example, the nano alumina filter media is formed into more than one layer. In yet another example, the nano alumina filter media is pleated.

The filter media may be used in a filtration system. In use, an air or gas stream is passed through the filter media and particulate matter is removed therefrom by retaining the particles in the filter media. In an example, the gaseous medium comprises a suspension of water droplets. Examples of use of the filter include, but are not limited to, use in room air filtration, use in respirators or face masks, use in automotive air filters, use in a clean room, use in an operating room, or use in an industrial setting, such as to remove paint or other particular matter contained in industrial mists. In an example, the filter media is used in an environment that has a humidity that is greater than about 75% RH.

EXAMPLES OF THE PRESENT INVENTION

The following examples illustrate several embodiments of the present invention. These examples should not be construed as limiting. All percentages are by weight. Calculations for determining pore size are provided in the discussion following that of Examples 1-10.

Example 1

The object of the experiments outlined below was to develop a nano alumina media having a pressure drop substantially equivalent to HEPA media and a filtration efficiency substantially higher than HEPA. It was also an object of the experiments to correlate the nano alumina filter media's water adsorption performance with that of a known HEPA filter media (hereinafter, "the Donaldson HEPA filter") to allow optimization of air filtration using water adsorption data.

Twenty four slurries of nano alumina on microglass mixtures were produced by reacting 5 μm diameter aluminum powder (Valimet Corp. #H-5) in water at 100° C. in the presence of mulched borosilicate glass fiber wool of random lengths (Lauscha). Non-woven fiber media containing nano alumina were formed on a 1×1 ft sheet mold and were strengthened with 17-23% bi-component fibers (Invista T104, 20 μm diameter, ½" length) that served as binder. Rhoplex binder was also added, about 2% by weight in liquid form. The sheets were labeled AF1-AF24.

The filters were tested as a single layer with an air stream having a flow velocity ranging from about 5.6 to about 23 m/min. The surface area available for filtration was about 8.2 $cm^2$. The filters were compared to the NanoCeram® water filter and the Donaldson HEPA filter in order to compare the characteristics of the inventive nano alumina air or gas filter to a water filter and a conventional HEPA filter.

Figure 13:
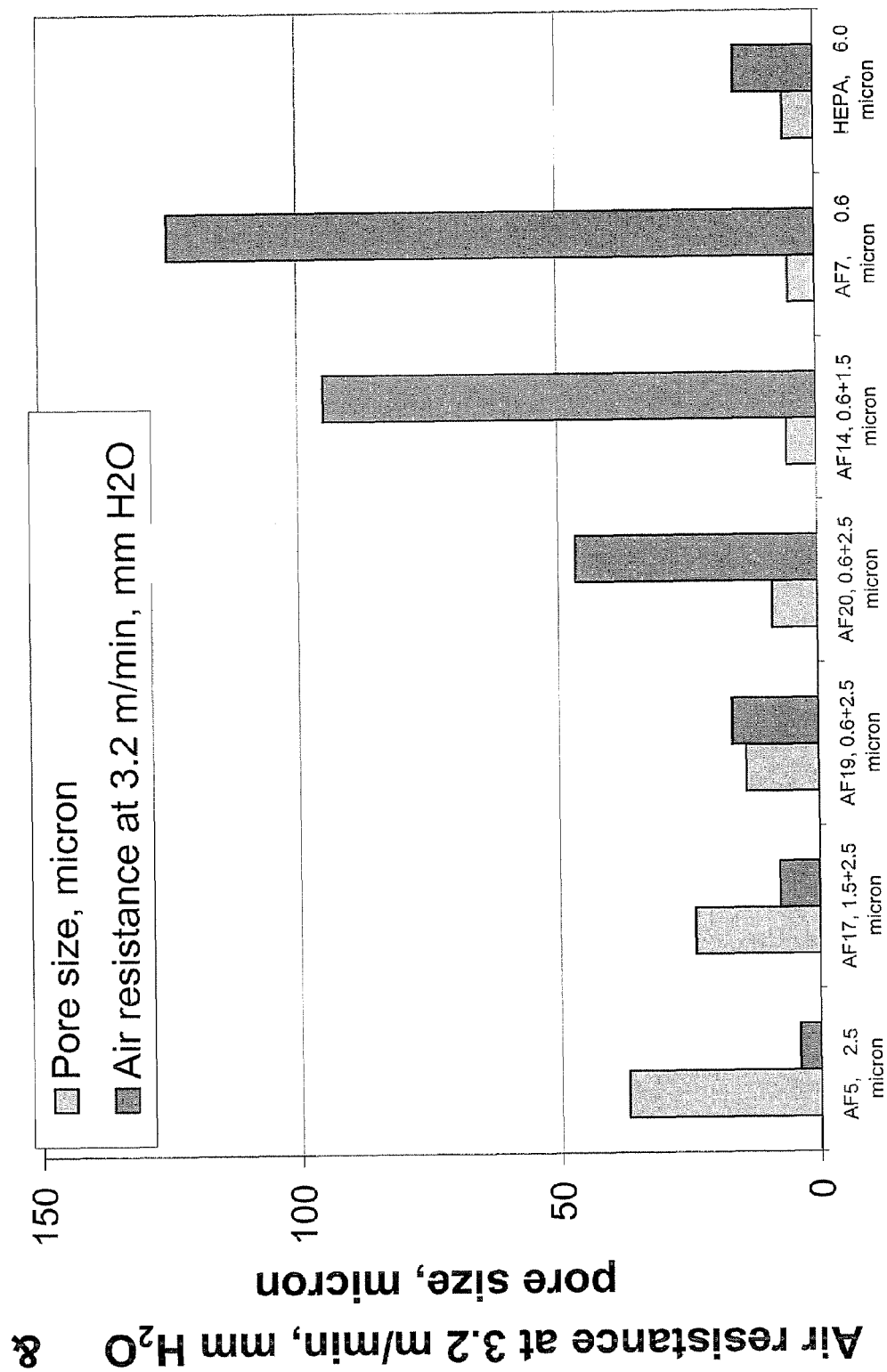
FIG. 13 is a graphical depiction of the relationship between the pressure drop and pore size as a function of fiber diameter.

Table 1 shows the composition, porosity, pressure drop, and average pore size for each hand sheet and the NanoCeram and HEPA media. FIG. 13 also shows the pore size and pressure drop for some of the nano alumina filters that were tested. Each filter media shown in Table 1 and FIG. 13 was tested as a single layer media. However, in use, performance may be improved by stacking more than one layer, as described above and as shown in the examples below.

As shown in Table 1, filters AF1-AF12 were comprised of nano alumina fibers mixed with microglass fibers of a single average diameter, either about 0.6 μm, about 1.5 μm, or about 2.5 μm. Filters AF13-AF24 were comprised of nano alumina fibers mixed with a combination of coarse and fine microglass fibers as follows: about 0.6 μm+about 1.5 μm; about 0.6 μm+about 2.5 μm; or about 1.5 μm+about 2.5 μm. The percentage of each fiber size comprising a given nano alumina filter media is indicated in Table 1.

further illustrated in FIG. 13. For example, media comprised of 0.6 μm microglass fibers had porosities of about 90% and pore sizes ranging from 4.2 to 10 μm. Media comprised of 1.5 μm microglass fibers had porosities of about 92.3% and pore sizes ranging from about 16 to about 21 μm. Finally, media comprised of 2.5 μm microglass fibers had porosities of about 95.3% and pore sizes ranging from about 35 to 38 μm.

The data of Table 1 and FIG. 13 also illustrate that media having the largest pore sizes or porosities also had the smallest pressure drops. For example, media having porosities of about 95% had pressure drops of about 3.4 to about 4.3 mm $H_2O$, in contrast to pressure drops of about 125 to about 204 mm $H_2O$ for porosities of about 90%.

In examples where the filter media was comprised of a combination of coarse and fine fibers, pore size was not

TABLE 1

Composition and Property of Nano Alumina Test Filters

| | % Nano Ceram | % bi-component fibers/ % cellulose | % glass micro Fibers | glass microfiber diameter, μm | Basis weight g/m² | Porosity, fraction | Air ΔP @3.2 m/min, mm $H_2O$ | Average pore size, (Eq. [3]), μm |
|---|---|---|---|---|---|---|---|---|
| Nano-Ceram | 35 | 13/21 | 31 | 0.6 | 160 | 0.88 | 130 | 3.8 |
| AF1 | 3.8 | 24/0 | 72.2 | 1.5 | 156 | 0.93 | 10.4 | 19 |
| AF2 | 11.7 | 22/0 | 66.3 | 1.5 | 170 | 0.92 | 12.3 | 17 |
| AF3 | 20 | 20/0 | 60 | 1.5 | 178 | 0.91 | 13.0 | 16 |
| AF4 | 3.8 | 24/0 | 72.2 | 2.5 | 155 | 0.95 | 4.1 | 35 |
| AF5 | 7.7 | 23/0 | 69.3 | 2.5 | 150 | 0.96 | 4.0 | 37 |
| AF6 | 11.7 | 22/0 | 66.3 | 2.5 | 160 | 0.96 | 4.3 | 38 |
| AF7 | 7.7 | 23/0 | 69.3 | 0.6 | 164 | 0.92 | 125 | 5.2 |
| AF8 | 20 | 20/0 | 60 | 0.6 | 198 | 0.90 | 151 | 4.8 |
| AF9 | 33.3 | 16.7/0 | 50 | 0.6 | 240 | 0.88 | 204 | 4.2 |
| AF10 | 11.7 | 22/13.3 | 53 | 1.5 | 164 | 0.93 | 10.4 | 21 |
| AF11 | 7.7 | 23/13.9 | 55.4 | 2.5 | 144 | 0.94 | 3.4 | 37 |
| AF12 | 20 | 20/12 | 48 | 0.6 | 178 | 0.90 | 134 | 5.1 |
| AF13 | 11.7 | 22/0 | 16.6<br>49.7 | 0.6<br>1.5 | 162 | 0.92 | 34.0 | 10 |
| AF14 | 11.7 | 22/0 | 33.2<br>33.1 | 0.6<br>1.5 | 168 | 0.91 | 95 | 5.7 |
| AF15 | 11.7 | 22/0 | 49.7<br>16.6 | 0.6<br>1.5 | 172 | 0.90 | 105 | 5.4 |
| AF16 | 7.7 | 23/0 | 17.3<br>52 | 1.5<br>2.5 | 160 | 0.94 | 5.7 | 28 |
| AF17 | 7.7 | 23/0 | 34.6<br>34.6 | 1.5<br>2.5 | 154 | 0.94 | 7.6 | 24 |
| AF18 | 7.7 | 23/0 | 52<br>17.3 | 1.5<br>2.5 | 160 | 0.94 | 9.2 | 22 |
| AF19 | 7.7 | 23/0 | 17.3<br>52 | 0.6<br>2.5 | 168 | 0.92 | 16.6 | 14 |
| AF20 | 7.7 | 23/0 | 34.6<br>34.6 | 0.6<br>2.5 | 158 | 0.90 | 46.6 | 8.7 |
| AF21 | 7.7 | 23/0 | 52<br>17.3 | 0.6<br>2.5 | 158 | 0.91 | 75.5 | 6.4 |
| AF22 | 11.7 | 22/13.3 | 26.5<br>26.5 | 0.6<br>1.5 | 168 | 0.92 | 48.2 | 8.8 |
| AF23 | 7.7 | 23/13.9 | 27.7<br>27.7 | 1.5<br>2.5 | 146 | 0.93 | 6.7 | 25 |
| AF24 | 7.7 | 23/13.9 | 26.5<br>26.5 | 0.6<br>2.5 | 156 | 0.90 | 43.3 | 8.5 |
| HEPA | NA | NA | NA | NA | 48 | 0.84 | 15.5 | 6.0 |

Note:
NA—not applicable

Relationship Between Microglass Fiber Diameter and Media Porosity

The data of Table 1 illustrate that media being comprised of microglass fibers having small diameters also had lower porosities and small pore sizes. These relationships are increased as dramatically as it was when the coarse fibers were present alone. See, e.g., Table 1 and FIG. 13. For example, 2.5 μm fibers combined with 1.5 μm fibers have pore sizes ranging from about 22-28 μm and porosities of about 94%, with a corresponding pressure drop of about 5.7 to about 9.2 mm $H_2O$.

Notably, the majority of samples AF1-AF24 had a pore size that is greater than the pore size in the Donaldson HEPA filter. For example, AF6 had a pore size that was more than six times greater than the Donaldson HEPA filter pore size.

Air-Flow Filtration Characteristics

Filters from the set of test filters AF1-AF24 were separated based on their airflow performance. The data for filters having a pressure drop of less than 10 mm $H_2O$ at 3.2 m/min are shown in FIG. 1. The solid line corresponds to a flow velocity of 3.2 m/min. The results show that there are several formulation variations of the claimed nano alumina fiber material that have a lower pressure drop than HEPA filters. These results are thought to be due to the larger pore size of the new filter media.

Evaluation of Filtration of Particulate Matter Using Monodisperse Latex Testing

Traditionally, oil based aerosols such as DOP (Di-octyl phthalate) have been used to simulate liquid aerosols, and sodium (NaCl) or potassium (KCl) chloride aerosols have been used to simulate solid particles when evaluating air filter material. The inventors compared the adsorption of ultrafine monodisperse latex spheres in water with that of HEPA filters and then attempted to establish a correlation based on data from DOP and NaCl tests. Specifically, air filters AF3 (average pore size 16 µm, see Table 1), AF6 (average pore size 38 µm), see Table 1, and the Donaldson HEPA filter, having a diameter of about 25 mm and an effective surface area of about 3.7 $cm^2$, were challenged with a fluid stream of clean (RO) water having 1 µm latex spheres at a constant flow rate of about 0.1 m/min. Although Table 1 describes filter media arranged in a single layer, stacks of one to four layers were used in this experiment in order to optimize performance of the filter media in air and water applications. Influent and effluent turbidity (in NTU or nephelometric turbidity units) in water was measured using a LaMotte Model 2020 turbidimeter.

Figure 2:
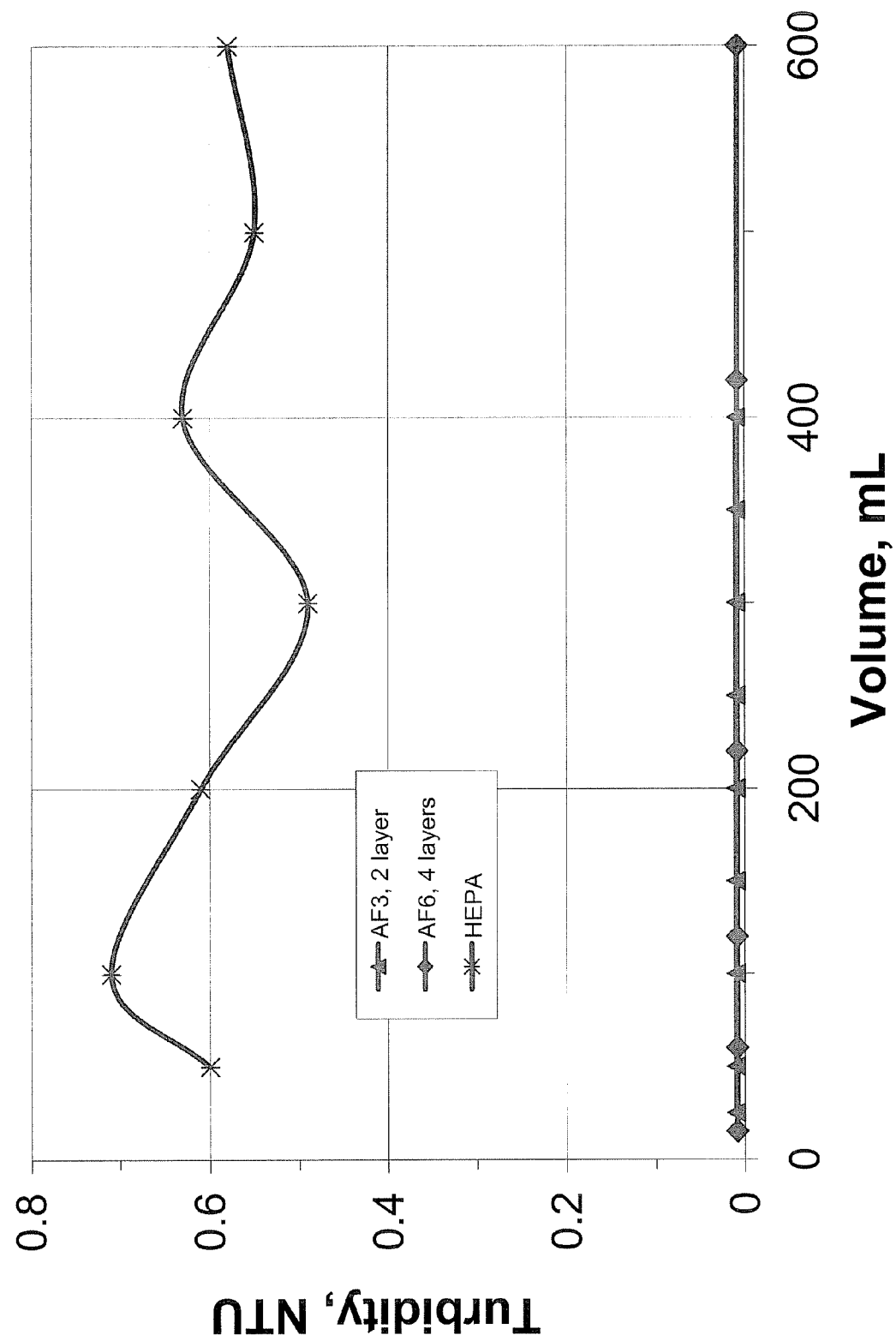
FIG. 2 is a graphical depiction of turbidity as a function of volume during filtration of 0.2 µm latex spheres suspended in water through the claimed nano alumina filters and a HEPA filter.

FIG. 2 shows a graphical depiction of the turbidity in the effluent leaving filters comprised of nano alumina and microglass fibers compared to a conventional HEPA filter. As shown, the inventive filters comprising the nano alumina and glass fibers exhibited virtually undetectable turbidity in the effluent compared to the HEPA filter.

The results of this experiment were surprising because the inventive filters retained 0.2 µm particles even though filters AF3 and AF16 had average pore sizes of about 16 and 38 µm, respectively. It was expected that filters having such large average pore sizes would not be able to retain particles that were so much smaller. The very poor retention of the HEPA filter in the water media was also surprising, indicating that HEPA filters have a much poorer particle retention in water than in air, and thus behave substantially differently in the two environments.

The objective of correlating water adsorption data to air performance was not successful and therefore air filter test data were relied on for subsequent experiments.

Examples 2-10

In Examples 2-10, the nano alumina filter media labeled AF3, AF6, AF11, and AF16 were used to further characterize the inventive nano alumina filter media as compared to the Donaldson HEPA filter. As set forth in Table 1, AF3 was comprised of 1.5 µm microglass fibers, AF6 and AF11 were comprised of 2.5 µn microglass fibers, and AF16 was comprised of a combination of 1.5 and 2.5 µm microglass fibers.

Example 2

Initial DOP and NaCl Initial Particle Penetration

Filters AF3 (average pore size 16 µm), AF6 (average pore size 38 µm), AF11 (average pore size 37 µm), and AF16 (average pore size 28 µm), manufactured in Example 1, and the HEPA filter, were sent to Nelson Laboratories in Salt Lake City, Utah, for DOP and neutralized monodisperse NaCl aerosol testing. The challenge concentration was $1.5 \cdot 10^6$ particles/$cm^3$ at 32 L/min through 100 $cm^2$ filters. The aerosols had a median particle size of 0.3 µm which were considered to be in the most penetrating size range. The test samples were prepared in the form of 10×10 cm squares or about 4-5" diameter discs. Three ply or three-layer flat sheets were tightened into the test device and challenged with an air stream at 32 L/min. The data are shown in Table 2.

TABLE 2

Initial Penetration of DOP and NaCl

| Sample | # plies | DOP/NaCl | Initial airflow resistance (mm $H_2O$) | Particle penetration, % |
|--------|---------|----------|-----------------------------------------|-------------------------|
| HEPA   | 1       | DOP      | 32.8                                    | 0.02                    |
|        |         | NaCl     | 32.8                                    | 0.025                   |
| AF16   | 3       | DOP      | 29.1                                    | 0.513                   |
|        |         | NaCl     | 32.1                                    | 0.323                   |
| AF6    | 4       | DOP      | 23.4                                    | 1.27                    |
|        |         | NaCl     | 23.6                                    | 0.755                   |
| AF11   | 4       | DOP      | 19.5                                    | 2.72                    |
|        |         | NaCl     | 19.4                                    | 1.60                    |
| AF3    | 1       | DOP      | 21.2                                    | 4.12                    |
|        |         | NaCl     | 21.3                                    | 2.61                    |

Filter AF16 had the lowest initial NaCl and DOP aerosol penetration, although even this penetration was not comparable to that of the HEPA filter. This sample is composed of a mixture of 1.5 and 2.5 micron microglass and contains only 7.7% nano alumina. It has a pore size of approximately 28 µm. The results show that many of the nano alumina formulations had an initial penetration higher than the HEPA specification.

Example 3

NaCl Aerosol Capacity Testing

Filters AF3, AF6, AF11, and AF16, and the HEPA filter (100 $cm^2$ test area) were challenged by the NaCl aerosol at a flow rate of 32 liters/min for approximately 3 hours each. About 0.0067 mg/min/$cm^2$ of NaCl was delivered to each filter, which is equivalent to about 40 mg/hr. As described above, typically three layers of AF16 (1.2 mm each, total of 3.6 mm) were necessary to achieve the equivalent pressure drop of the HEPA, so the testing was done with three layers vs. HEPA.

Figure 3:
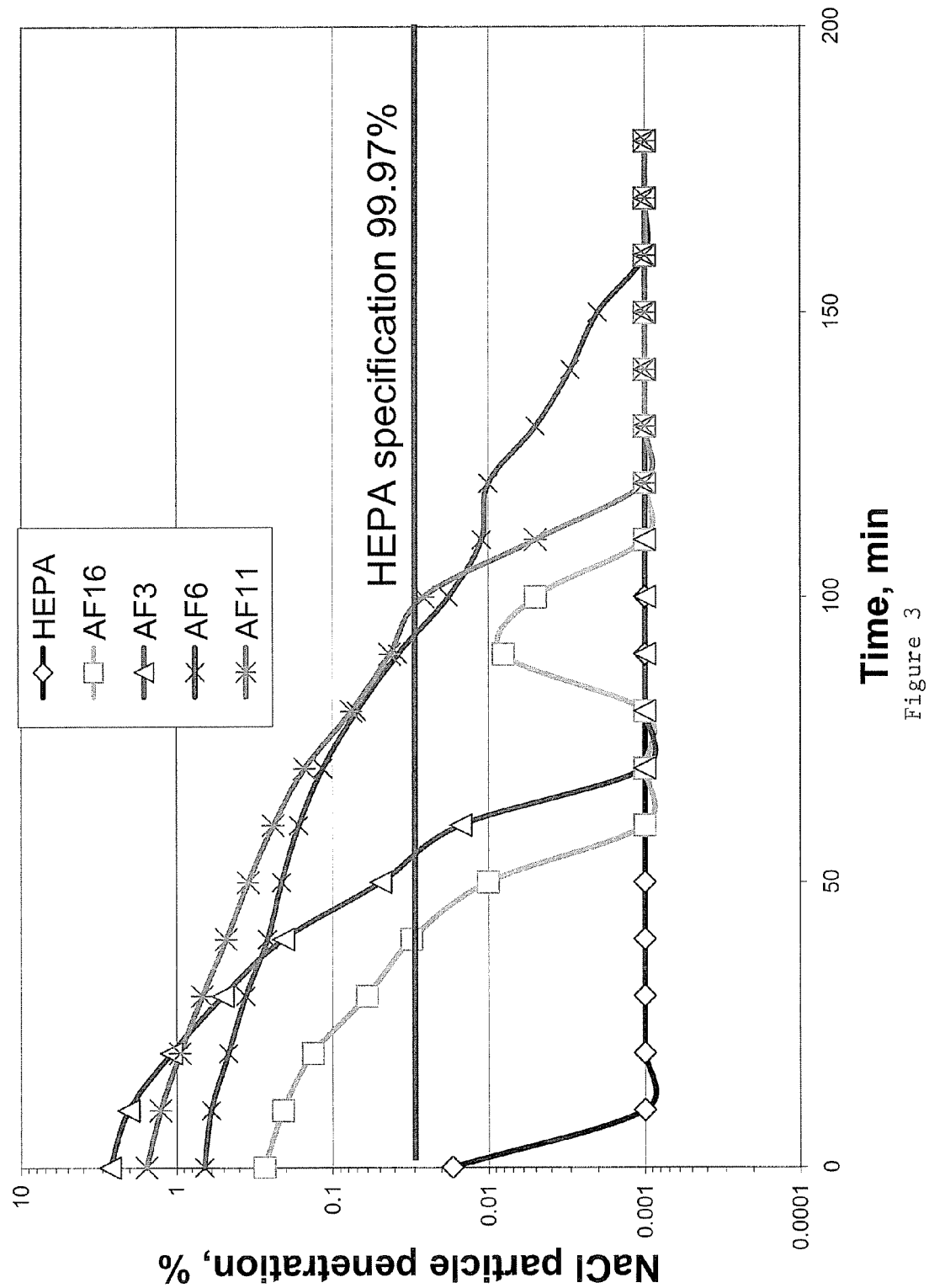
FIG. 3 is a graphical depiction of penetration of the claimed nano alumina and HEPA filters while continuously challenging them with 0.3 µm NaCl aerosols.

FIG. 3 shows a graphical depiction of the penetration of each filter tested by NaCl aerosols as a function of time. As shown, filter AF16 had the lowest initial NaCl aerosol penetration but was still considerably above that of the HEPA. AF16 had the lowest initial penetration and was therefore used for further evaluation.

Capacity

Figure 4:
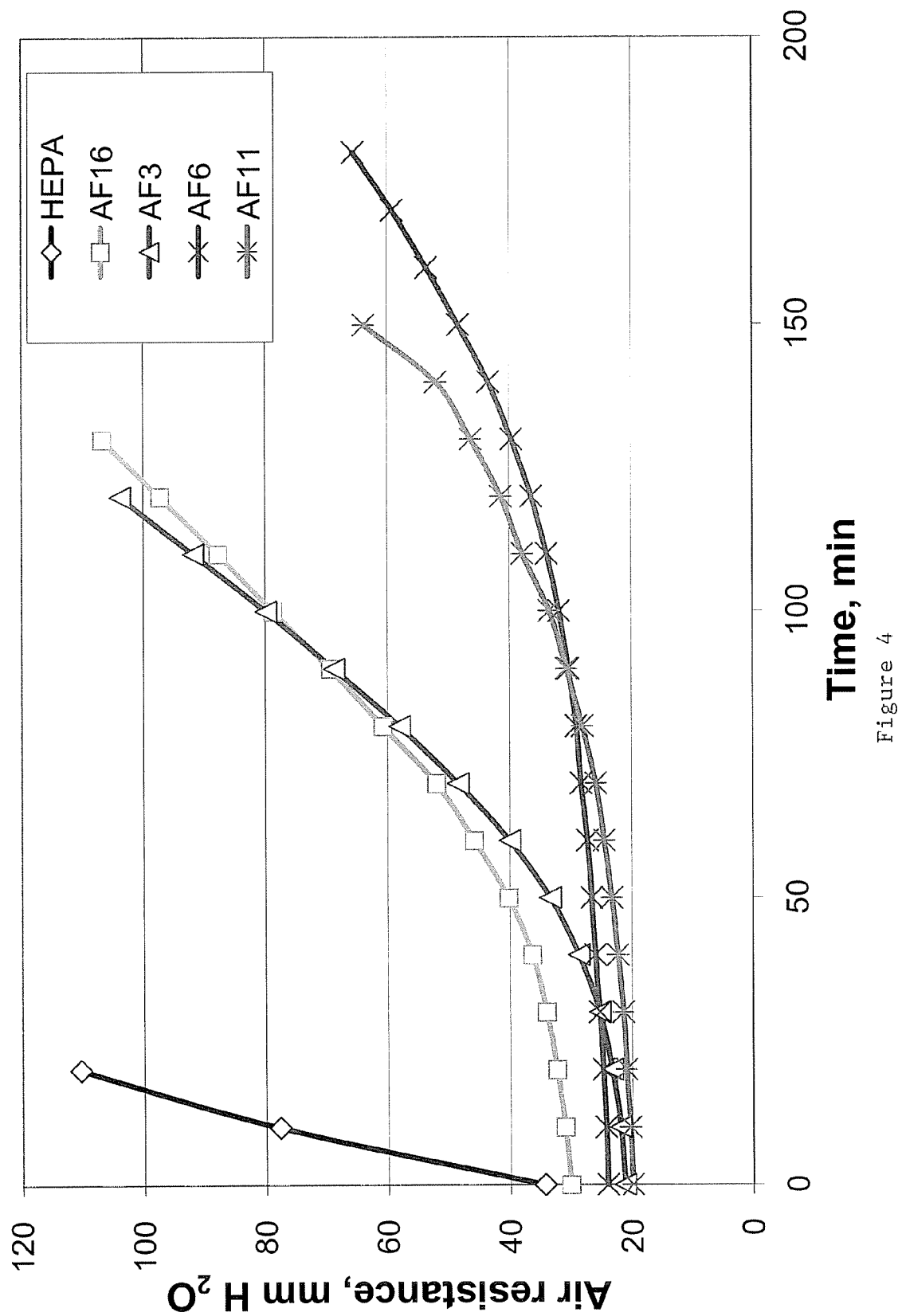
FIG. 4 is a graphical depiction of air resistance of the claimed nano alumina and HEPA filters while continuously challenging them with 0.3 µm NaCl aerosols.

FIG. 4 shows a graphical depiction of the air resistance of the filters as a function of time. Capacity (or filter life) in this example is defined as the time (minutes) required to reach a pressure drop (ΔP) of 50 mm H$_2$O. As shown in FIG. 4, all of the inventive nano alumina filters tested had a capacity that is at least ten times that of the HEPA filter. Filters AF6 and AF11 have capacities that exceeded that of HEPA by a factor of about 30 times. These data are important because the "lifetime" of a filter is typically defined according to a selected limiting pressure drop across the filter. The pressure buildup across the filter defines the lifetime at a defined level for that application or design. Since the buildup of pressure is a result of load, for systems of equal efficiency, a longer life is typically directly associated with a higher capacity. Efficiency is the propensity of the media to trap rather than pass particulates. Typically the more efficient a filter media is at removing particulates from a gas flow stream, in general the more rapidly the filter media will approach the "lifetime" pressure differential assuming other variables are held constant.

A filter having an increased capacity is of considerable benefit because it reduces the cost of frequent filter change-outs. Additionally, many filters, including those that intercept bacteria and viruses or nuclear materials, have to be disposed of as hazardous waste. Therefore, reducing the frequency with which hazardous waste filters have to be changed and disposed of is a further economic benefit.

Table 3 presents results of the NaCl aerosol tests at air flow rates of about 3.2 m/min for filters disclosed in U.S. Pat. No. 6,872,431 to Kohlbaugh ("the '431 patent") and the inventive fibers comprising nano alumina and microglass fibers at a "pre-HEPA" level for removal of 0.3 μm particles, wherein "pre-HEPA" is defined as a media efficiency ranging from about 98.9% to about 99.6%. Table 3 also presents the results of challenging one of the inventive filters (a single layer of filter AF16) with the most penetrated particle size of 0.33-0.40 μm of neutralized KCl at a flow rate of about 4.6 m/min.

The results shown in Table 3 indicate that at the "pre-HEPA" level:

1. The AF6 media, which is pleatable, has greater capacity to reach a pressure drop of about 125 mm H$_2$O and about 50 mm H$_2$O compared to the media disclosed in the '431 patent incorporating either 10, 14, or 25 layers. The life expectancy at 125 and 50 mm H$_2$O is improved by about 40%, 28%, and 20%, respectively.
2. A single layer of AF16 media has a life expectancy and removal efficiency of the most penetrating particles (KCl, 0.33-0.4 μm) that exceeds that of the filters disclosed in the '431 patent for 10 and 14 layer composites.

These data are important because they show that the nano alumina fiber media has an increased life expectancy compared to the '431 filter and because their removal efficiency of particles exceeds that of the '431 filter. Thus, not only are the claimed nano alumina filters more cost-effective, they also perform better. Additionally, it is much less costly to manufacture a single media than one with 10-14 different layers, and in the latter case, one has to worry about delamination.

Table 4 presents results of the NaCl aerosol tests at air flow rates of about 3.2 m/min for filters disclosed in the '431 patent and the inventive fibers comprising nano alumina and microglass fibers at a HEPA level for removal of 0.3 μm particles.

TABLE 3

NaCl (0.3 μm) Aerosol Penetration of Test Samples at "pre-HEPA"[b] Level

| Media | Initial particle penetration % | Number of Layers | Single layer efficiency % | Thickness, mm | Time to 125 mm H$_2$O, min | Time to 50 mm H$_2$O, min |
|---|---|---|---|---|---|---|
| U.S. Pat. No. 6,872,431 | 0.6[a] | 10 | 40 | 0.54[b] | <170[c] | <80[c] |
| U.S. Pat. No. 6,872,431 | 0.4[d] | 14 | 28 | 0.75[b] | <230[c] | <125[c] |
| U.S. Pat. No. 6,872,431 | 0.4[a] | 25 | 20 | 1.4[b,e] | <260[c] | <170[c] |
| AF6 | 0.76 | 4 | 80[f] | 1.8 | 320[f] | 160 |
| AF16 | 1.1[g] | 1 | 98.9[g] | 1.2 | 170[f] | 100[f] |

Notes:

[a]this is an estimated values based on the equations on the disclosure of the '431 patent, pages 23–24;

[b]these are estimated values based on the data disclosed in the '431 patent page 35, lines 1–10;

[c]these are estimated value based on data disclosed in the '431 patent, page 43,

[d]this is an estimated value based on data disclosed in the '431 patent, page 39,

[e]the estimated thickness exceeds the limit for filter media construction (see claim 14, the '431 patent);

[f]these are estimated values;

[g]this filter was challenged with the most penetrated particle size of about 0.33 to about 0.40 μm of neutralized KCl at about 4.6 m/min.

TABLE 4

Results of NaCl Aerosol Tests at a HEPA Level

| Media | Composite efficiency, % | Number of Layers | Single layer efficiency, % | Thickness, mm | Time to 125 mm H$_2$O, min | Time to 50 mm H$_2$O, min |
|---|---|---|---|---|---|---|
| U.S. Pat. No. 6,872,431 | 99.97[a] | 16 | 40 | 0.89[b] | <170[c] | <80[c] |
| U.S. Pat. No. 6,872,431 | 99.97[a] | 25 | 28 | 1.4[b] | <230[c] | <125[c] |
| AF6 | 99.97[d] | 5 | 80[d] | 1.8 | 300[d] | 120[d] |
| AF11 | 99.976[d] | 6 | 75[d] | 2.5 | 310[d] | 120[d] |
| Donaldson HEPA | 99.975 | 1 | 99.975 | 0.2 | 24 | 3.5 |

Notes:
[a] these are estimated values based on the equations disclosed in the '431 patent, pages 23–24;
[b] these are estimated values based on the data disclosed in the '431 patent page 35, lines 1–10 (note that the estimated thickness exceeds the limit for filter the media construction, per claim 14 of the '431 patent);
[c] this is an estimated value based on data disclosed in the '431 patent, page 39, lines 39–45;
[d] this is an estimated value.

The data shown in Table 4 indicate that the AF6 and AF11 media have greater capacities to reach a pressure drop of 125 or 50 mm H$_2$O compared to the media disclosed in the '431 patent that has 16 or 25 layers. The inventive media improves the life expectancy of the filter by at least 80% to 125 mm H$_2$O terminal pressure with respect to the '431 patent's media, although the '431 patent's media having 25 layers has a comparable life expectancy to a pressure drop of 50 mm H$_2$O.

Example 4

Preconditioning

The objective of this example was to eliminate the initial leakage when tested to a HEPA protocol. It was hypothesized that the largest pore sizes in the filter media (which contains a wide range of pore sizes because of the asymmetric fiber arrangement) were responsible for the initial leakage. It was further hypothesized that injection of a foreign particle into the filter to condition the filter prior to use would flow into the largest of pores, blocking them and thereby reducing this leakage to improve the filter's efficiency.

In order to test this hypothesis, the filters were pre-loaded with a conditioning agent so that pores were plugged prior to use. Sample AF16 (25 mm diameter filter) was used in this test. Monodisperse latex spheres (Duke Scientific) were used to condition the filters because these spheres are stable in air and not affected by a humid air stream. Experiments were carried out in which latex spheres had diameters of either 0.2, 0.5, or 1 μm. The spheres were loaded onto the filter and the air resistance was measured.

Air flow resistance was measured as described above. Preloading with 0.2 μm spheres had minimal effects on the pressure drop in the inventive filters (data not shown) and after some pre-loading the turbidity of the effluent was measurable.

Figure 5:
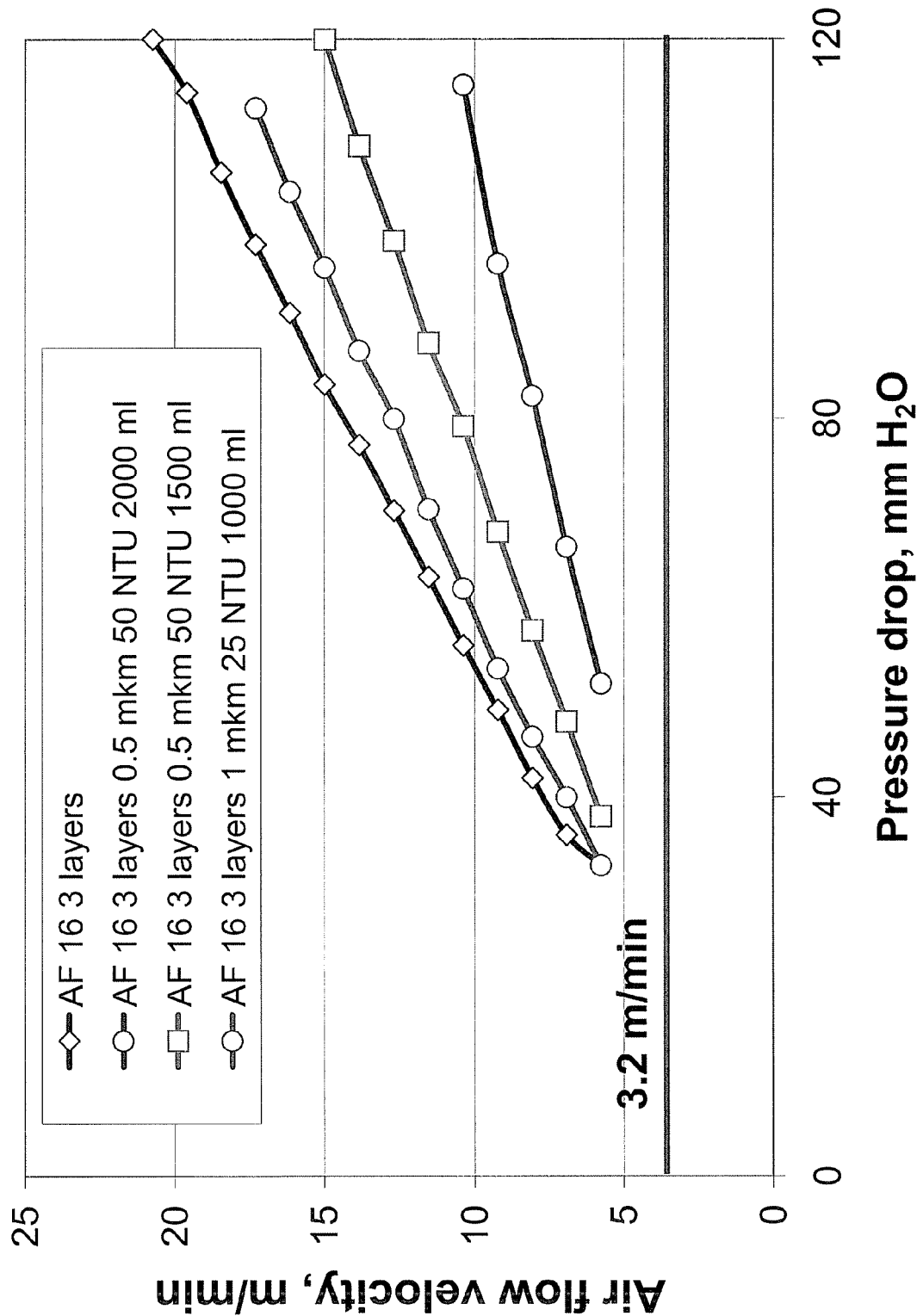
FIG. 5 is a graphical depiction of air flow velocity vs. pressure drop through the claimed nano alumina filters after being preconditioned with 0.5 and 1 µm latex spheres.

FIG. 5 is a graphical depiction of the air velocity and change in pressure after pre-loading the inventive filters with 0.5 or 1 μm latex spheres. During pre-loading, it was noted that the turbidity of the effluent was below the detection limit of 0.01 NTU, suggesting quantitative adsorption of these larger particles by the filter media. The data suggest that 0.5 and 1 μm latex spheres are suitable for pre-conditioning the filters with spheres.

In summary, the results of Example 4 show that:
1. Foreign particulates such as monodispersed particulates can be used to condition nano alumina filter media.
2. Measurement of the turbidity during preloading is an effective way to monitor and control the preloading process.
3. Samples can be loaded with 0.5 and 1 μm latex beads to mirror the pressure drop (ΔP) that occurs during NaCl aerosol testing.
4. The 0.2 μm latex particle is too small to achieve the desired ΔP.

As an alternative to the costly latex particles, less costly and preferably sub-micron particles, may be used to precondition the filters, including for example, ultrafine granular carbon, fumed silica agglomerates (Cab-O-Sil), or metal oxides.

Example 5

NaCl Penetration and Capacity Testing for Preloaded AF16 Samples

Test samples were prepared by preloading 0.5 μm latex spheres onto one face of a filter consisting of 3 layers of AF16 media. The media was prepared as circular discs with an area of 175 cm$^2$. The samples (100 cm$^2$ test area) were challenged (at Nelson Laboratories) with an NaCl aerosol at a flow rate of 32 liters/min for approximately 3 hours each. The approximate mass of NaCl that was delivered to the filter was 0.0067 mg/min/cm$^2$, or 40 mg/hr or 0.5%/hr of the exposed mass of the filter. At a flow rate of 32 liters/min, the velocity was 3.2 m/min. Filter thickness of three layers AF16 was about 0.36 cm, resulting in a computed residence time of about 0.07 sec.

Figure 6:
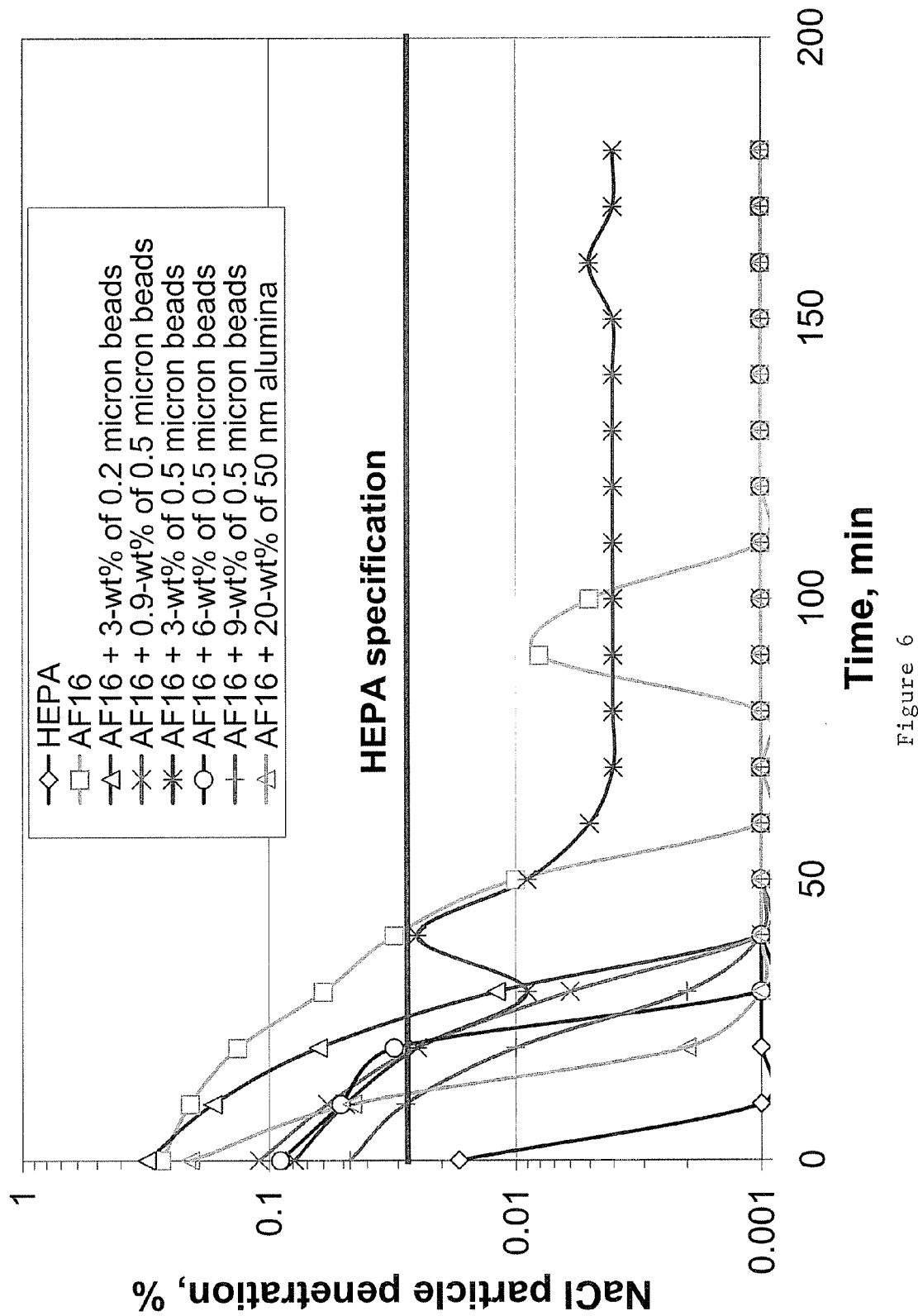
FIG. 6 is a graphical depiction of the penetration of the claimed nano alumina filters preconditioned with latex beads compared to a nano alumina filter without preconditioning and a HEPA filter when penetrated by 0.3 µm NaCl aerosols.

FIG. 6 shows a graphical depiction of the air resistance of nano alumina filters preconditioned with latex spheres during NaCl loading. As shown, over the 3 hours of test, the air resistance of all of the nano alumina test samples was much lower than that of HEPA. The HEPA filter reached a ΔP of 50 mm H$_2$O in about 4 minutes, while the nano alumina samples took about 40 minutes to reach the same ΔP (one nano alumina filter that contained 9 wt % latex reached a ΔP of 50 mm H$_2$O in about 30 minutes). This improvement in the filter life, which is about 7-10 ten times greater than HEPA, is a benefit for applications that use high efficiency filters, including hospital, military collective protection, homeland security, automotive and respirator filters.

Figure 7:
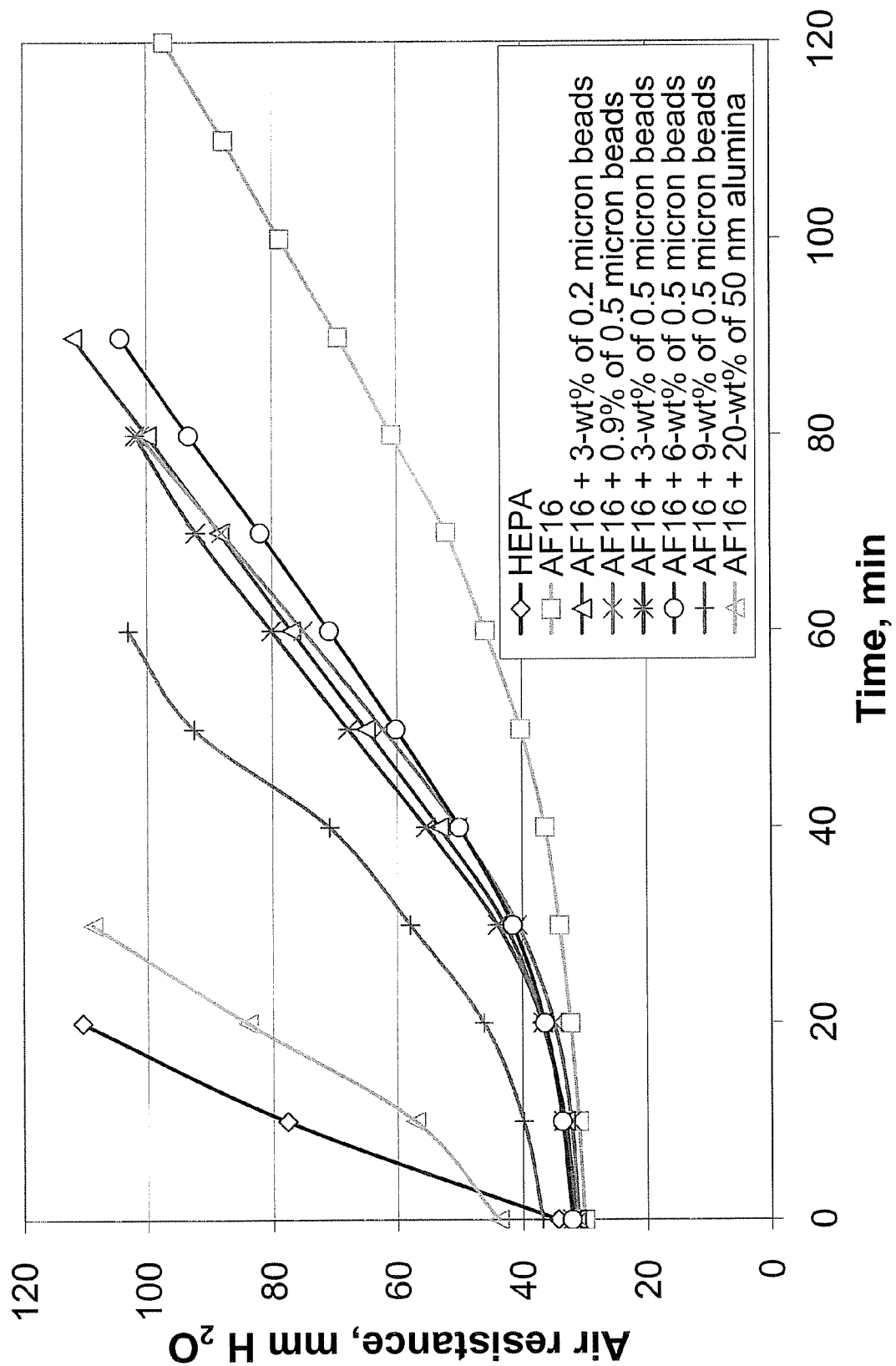
FIG. 7 is a graphical depiction of the air resistance of the claimed nano alumina filters preconditioned with latex beads compared to that of a nano alumina filter without preconditioning and a HEPA filter.

FIG. 7 shows a graphical depiction of the NaCl penetration of nano alumina filters preconditioned with latex beads. Although the initial penetration was not reduced to 0.03%, the retention increased with continued loading of the NaCl particles. All of the pre-conditioned AF16 samples had lower initial NaCl penetration than AF16 itself. There is a trend towards better performance with increased preloading of 0.5 μm latex beads, with the lowest value being 0.047% penetration for 9 wt % latex as compared to the 0.03% penetration that defines HEPA.

Example 6

Figure 8:
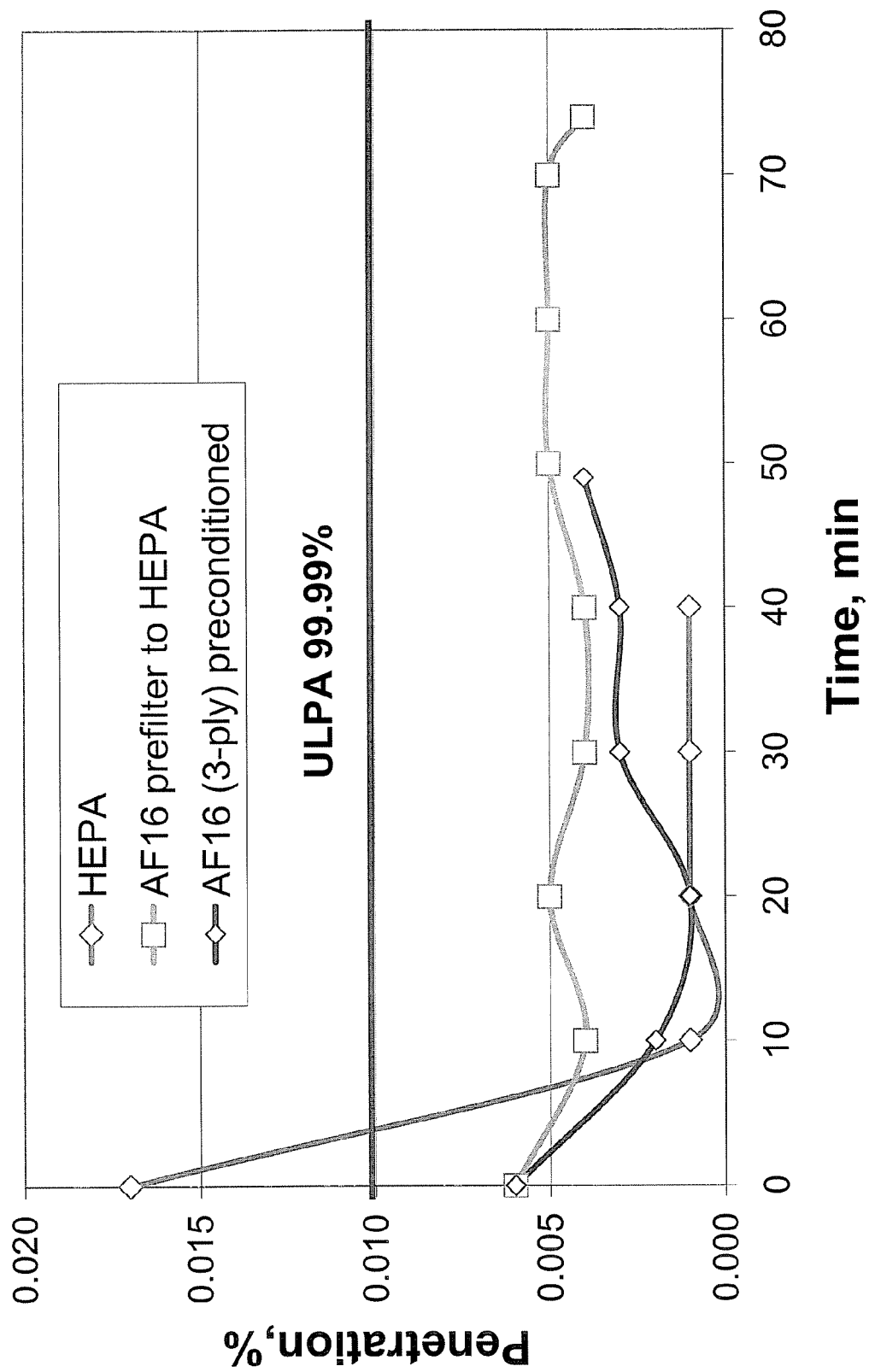
FIG. 8 is a graphical depiction of the penetration of 0.3 µm NaCl aerosols through the claimed nano alumina filters and a HEPA filter.

Filter media were tested for NaCl aerosol retention at Nelson Laboratories as in Example 2. FIG. 8 shows a graphical depiction of the penetration of 0.3 μm NaCl aerosols through test media. In this example, the following samples were compared: HEPA; a single layer of AF16 without preloading that was used as a prefilter for the HEPA filter; and three layers of AF16, preconditioned with latex particles. As shown, the HEPA only filter could not be rated as an ULPA. In contrast, the preconditioned AF16 filter had an initial and continued retention of >99.99%, thereby qualifying it as an ULPA filter. Additionally, as shown in FIG. 8, adding a single layer of AF16 (not preconditioned) as a prefilter to the HEPA also resulted in an ULPA rating. These data show that the claimed nano alumina filter media have a retention that exceed that of conventional HEPA filters such as the Donaldson HEPA filter, and that using nano alumina as a prefilter increases the HEPA rating to an ULPA rating.

Figure 9:
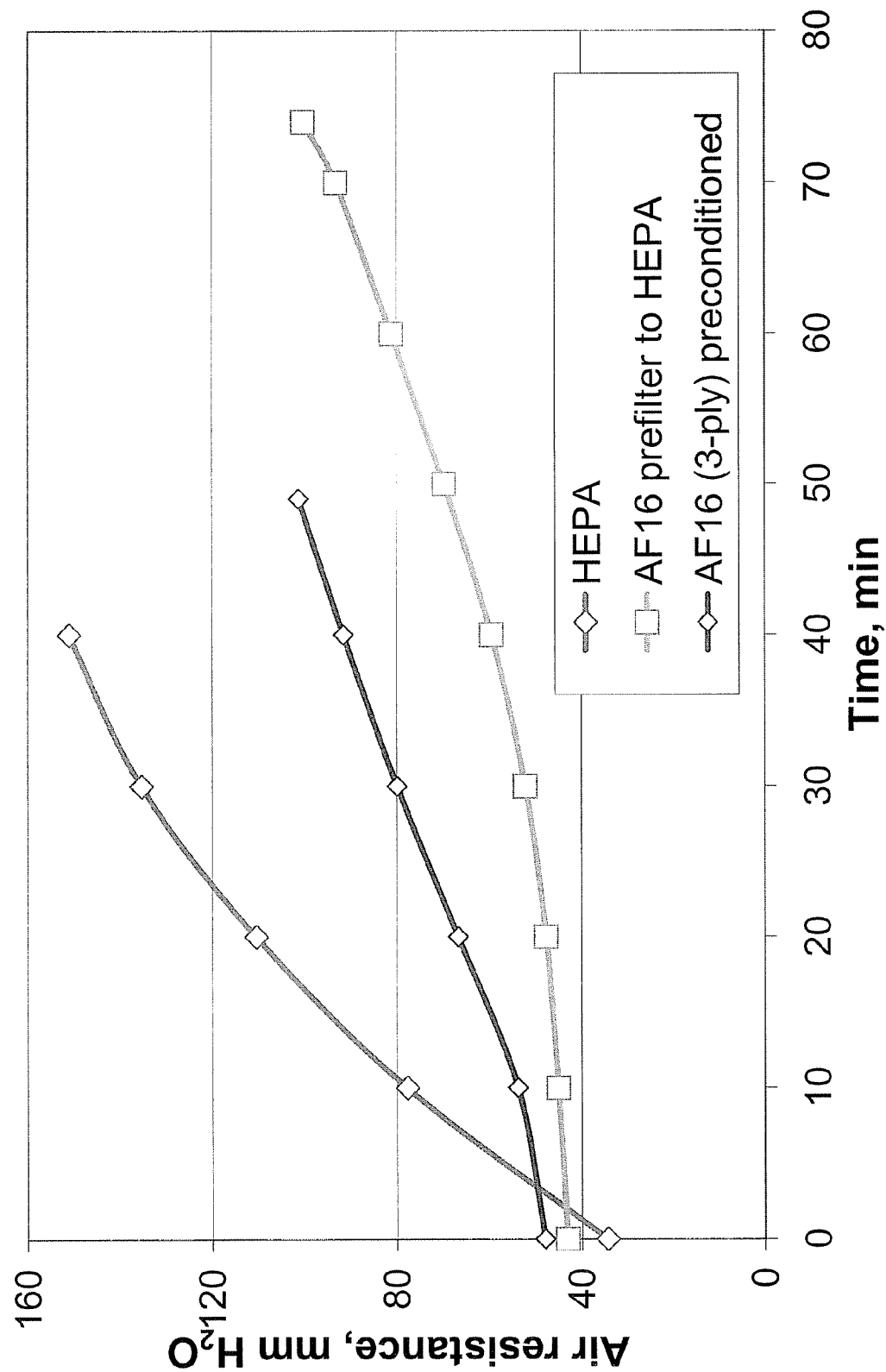
FIG. 9 is a graphical depiction of the air resistance of the claimed nano alumina filters and a HEPA filter during NaCl aerosol capacity testing.

FIG. 9 shows a graphical depiction of the air resistance of the test filters during NaCl aerosol capacity test for the samples described above. The addition of a single layer of AF16 without preconditioning extended the life of the HEPA filter by about 700%, to a 50 mm ΔP threshold, which would result in considerable savings if used in practice.

Thus, the claimed filters are more effective at retaining particles and have a greater life expectancy than conventional HEPA filters and therefore these claimed nano alumina filter media are more cost-effective.

Example 7

Samples of AF16 media were tested at LMS Technologies, Inc. (Edina, Minn.) in accordance with EPA Method 319 regulations that are specific for measuring filtration systems for paint overspray arrestance in the aerospace industry. In U.S. industrial finishing operations, 30% of paint that is sprayed, amounting to 90 million gallons, is overspray, with much of this dispersed into the atmosphere.

Figure 10:
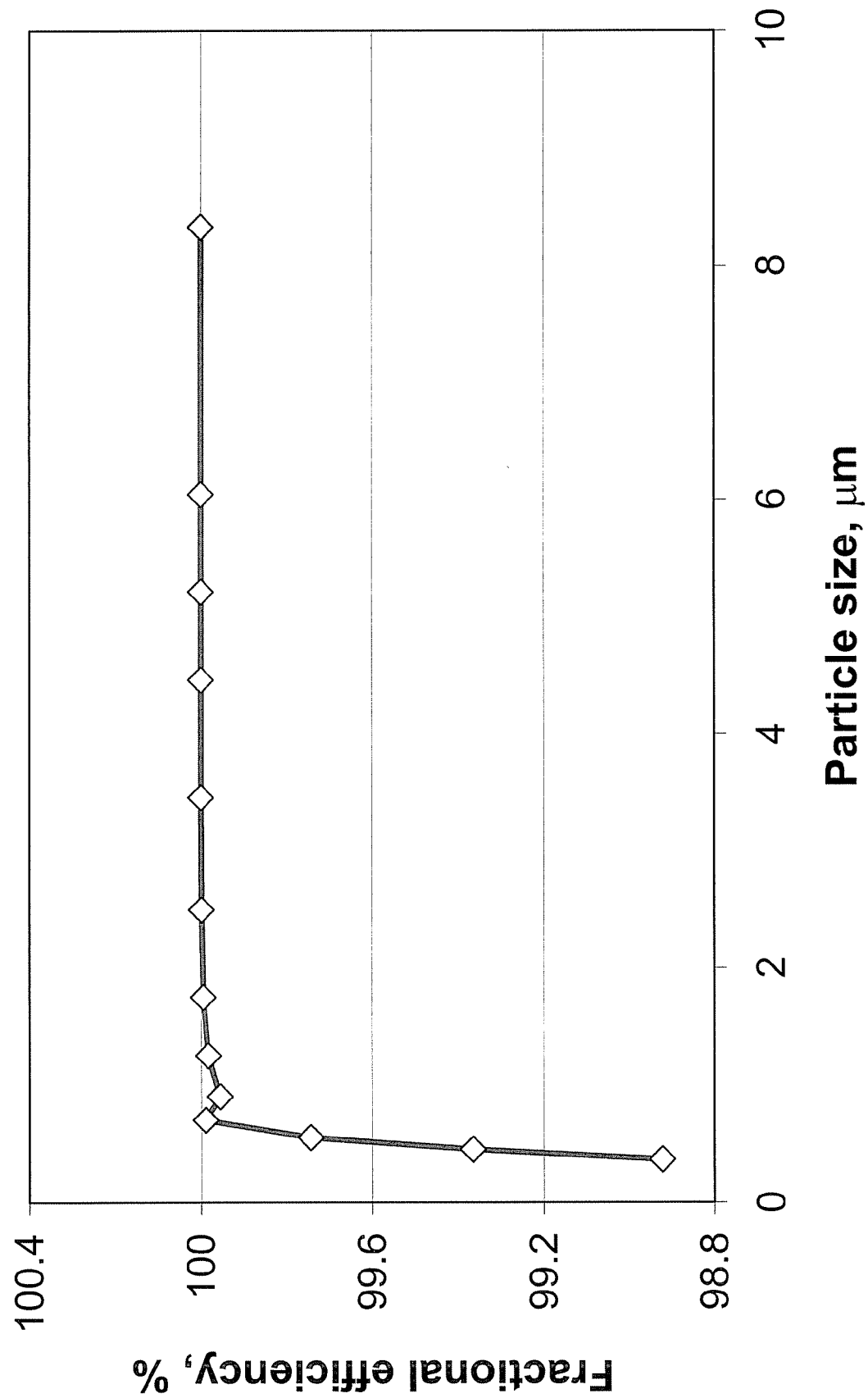
FIG. 10 is a graphical depiction of fractional efficiency of the claimed nano alumina filters as a function of particle size of aerosolized KCl droplets.

One layer of AF16 media was tested at a flow velocity of 15 fpm. The initial pressure drop was 22 mm H₂O. FIG. 10 shows a graphical representation of the retention or fractional efficiency of a test filter as a function of particle size. These same data are presented in Table 5.

Figure 14:
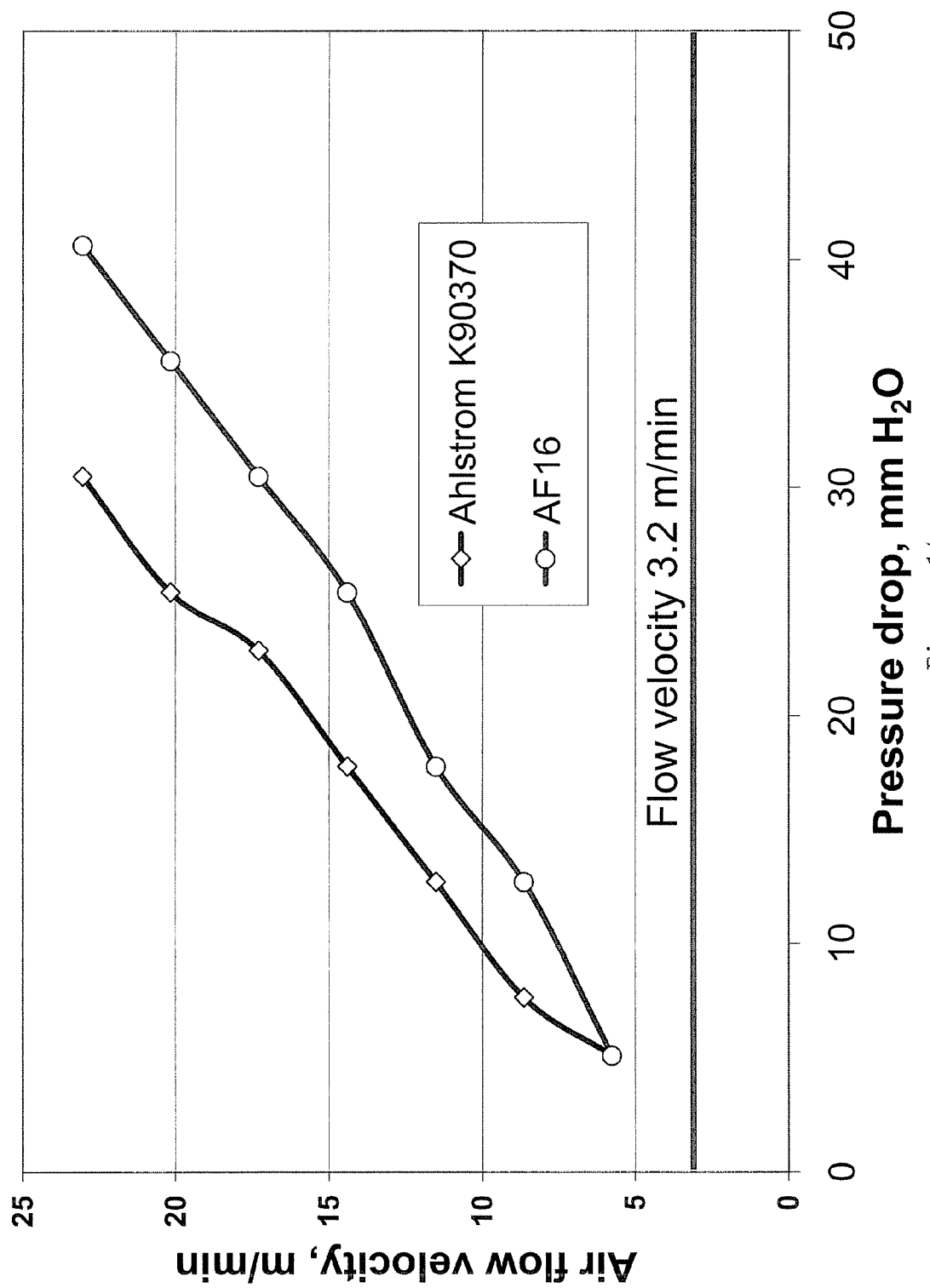
FIG. 14 is a comparison of pressure drop of the claimed nano alumina filter media and a sub-HEPA filter.

The filter was also compared to a commercial sub-HEPA filter (Trinitex K903-70, manufactured by Ahlstrom). FIG. 14 compares the pressure drop of the Trinitex filter to that of filter AF16. As shown, the pressure drop across the two filters is very similar. Importantly, the retention by the AF16 was extraordinarily better than the EPA specification as well as the Ahlstrom media over all particle size ranges of the comparison. The data show that the new media can substantially improve the performance of sub-HEPA media without requiring preconditioning.

TABLE 5

Retention of KCl aerosols as a function of particle size

| Size range (μm) | Initial retention by one layer of nano alumina filter media AF16 (%) | EPA 319 Specification | Ahlstrom Trinitex |
|---|---|---|---|
| 0.33–0.40 | 98.923 | | 52% |
| 0.40–0.50 | 99.365 | >75% | 59% |
| 0.50–0.60 | 99.743 | | 63% |
| 0.60–0.80 | 99.989 | >85% | 68% |
| 0.80–1.00 | 99.955 | | 74% |
| 1.00–1.50 | 99.983 | | 90% |
| 1.50–2.00 | 99.995 | >95% | 95% |

Example 8

A co-pending patent application addresses the use of silver in controlling the proliferation of bacteria. Therefore, the inclusion of silver in the air filtration media was tested here. Three nano alumina handsheets were prepared from aluminum powder as described for sample HF0404 in example 1, with the exception that silver nitrate (0.1%, 0.3% and 1 wt % as silver to the dry weight of the slurry) was added to the slurry. Samples (25 mm diameter) were mounted in a filter holder and were loaded with 10 ml of 8·10⁷ CFU/ml of Klebsiella terrigena suspension in buffered water solution. Bacteria were eluted from the filters in reverse direction with 3 ml of solution containing 3% beef extract and 0.35% glycine solution at pH 7.5 immediately after loading and then after 1, 5, and 18 hours of dwell.

Figure 11:
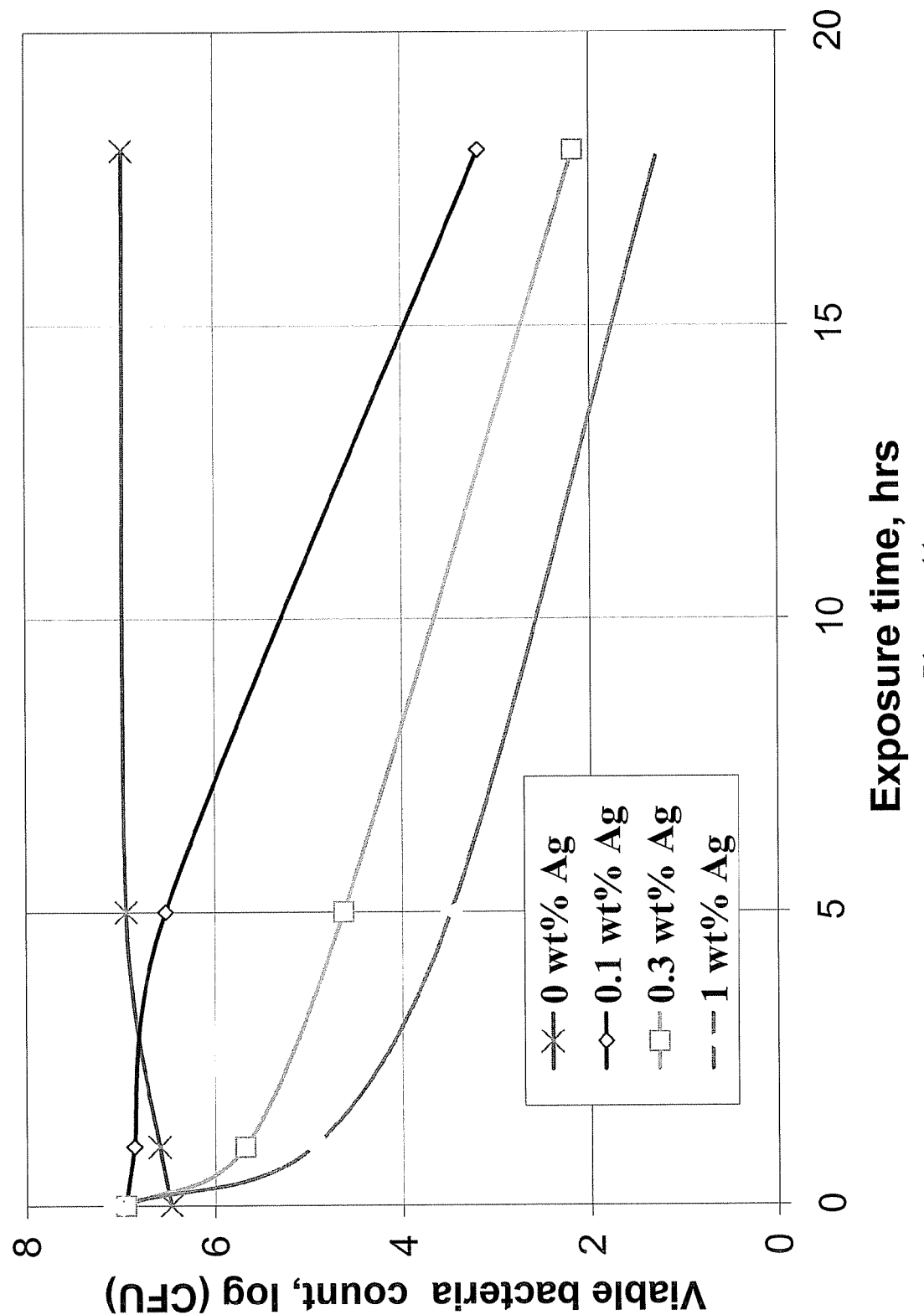
FIG. 11 is a graphical depiction of the antimicrobial effect of the claimed silver impregnated nano alumina filters on bacterial proliferation.

FIG. 11 shows a graphical depiction of the antimicrobial effect of the inclusion of ionic silver on nano alumina fibers as a function of time of exposure to the filter. As shown, silver impregnated nano alumina filters controls bacterial proliferation, with improved control as the percent silver nitrate increased.

Tests also showed that 1% silver had no discernable affect on filtering MS2 virus, demonstrating that the virus efficiency of the filter media was not affected after adsorption of the 1% silver.

These results show that addition of silver nitrate to the filter minimizes any re-entrainment of bacteria or virus off the filter because it acts as an antimicrobial agent. The effluent of silver from filters that had been impregnated was about 30 μg/L, substantially below the 100 μg/L required by the EPA for drinking water. Once used, the filter can be disposed of as sanitary waste rather than costly hazardous waste.

Example 9

Testing Media Samples with Aerosolized E. Coli Bacteria

Figure 12:
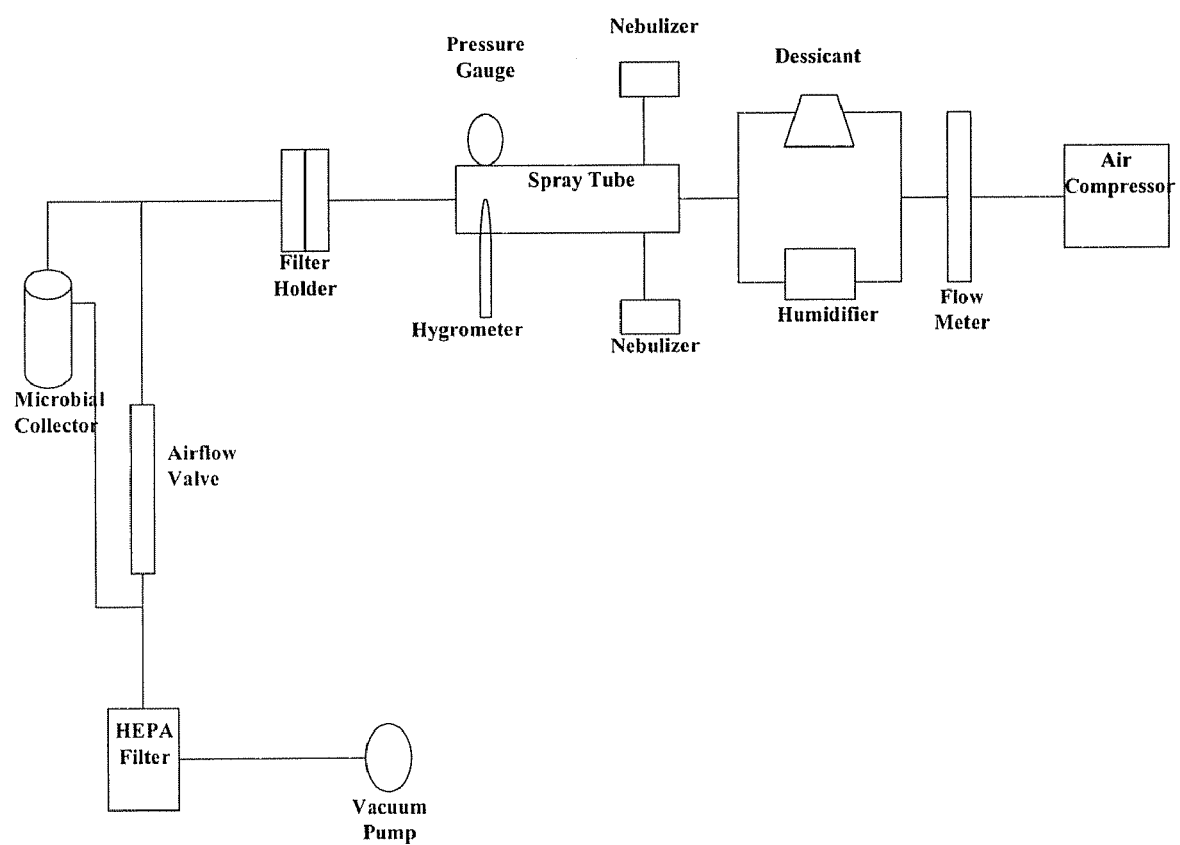
FIG. 12 is a schematic of the system used to challenge the claimed nano alumina filters with waterborne bacterial aerosols.

An apparatus originally developed by Henderson [1] has been assembled and tested with *E. coli* bacteria. In the apparatus, a schematic of which is shown in FIG. 12, 5 ml of *E. coli* $1.4 \cdot 10^9$ CFU/ml suspension in buffer solution was nebulized by a DeVilbiss PulmoMate Nebulizer (Model SR4650D). A second nebulizer was operated with an equal amount of buffer solution. The generated aerosols were injected into a 5 cm diameter, 90 cm long tube. The relative humidity was adjusted by mixing air that passed through the wet and dry anus of the air conditioner before entering the spraying tube. The relative humidity and temperature of the air close to the end of the tube were measured by a humidity meter. Approximately ⅓ of the flow from the outlet of the aerosol tube was passed through the AGI-30 impinger. The rest of the flow was passed through the 12 mm inner diameter tubing and was then combined with the air escaping through the impinger. The air flow was passed through the HEPA filter (Whatman, PolyVent-1000 Cat #6713-1075).

Total flow was 38 liters of air per minute. Two nebulizers produced the airflow of 12 L/min (6 L/min each) and 26 L/min of the airflow was supplied by the air compressor. Airflow through the impinger was 12 L/min.

Filter efficiency was calculated as:

$$\% \text{ Efficiency} = \frac{(\text{Upstream } E.coli \text{ concentration} - \text{Downstream } E.coli \text{ concentration})}{\text{Upstream } E.coli \text{ concentration}} \times 100\% \quad [1]$$

where the upstream *E. coli* concentration was determined without the filter in the *E. coli* laden airstream and the downstream *E. coli* concentration was determined with the filter in the *E. coli* laden airstream, at or near 100% relative humidity.

In the first experiment three layers of the AF16 filter media (not preconditioned with particles) was assembled into a 90 mm diameter filter holder. In the second experiment, one layer of Donaldson HEPA was assembled into the same filter holder. As shown in Table 6, the AF16 filter media had a retention of the bacteria that was about 50 times greater than that of the HEPA filter.

TABLE 6

Percentage efficiency of nano alumina filter against aerosolized *E. coli* challenge (Condition - 32 LPM, 100% RH, Temperature 23.9° C.)

| Filter media | Thickness, mm, (# plies thickness) | Average Pore size,* μm | Filter/ No filter | Number of *E. coli* bacteria determined in AGI-30 buffer solution, CFU | *E. coli* retention efficiency, % |
|---|---|---|---|---|---|
| AF16 | 3.6 (=3 × 1.2) | 28 | Filter | <1 | >99.9998 |
|  |  |  | No Filter | $5.9 \cdot 10^5$ |  |
| AF6 | 7.2 (=4 × 1.8) | 38 | Filter | <4 | >99.9992 |
|  |  |  | No Filter | $5.2 \cdot 10^5$ |  |
| AF3 | 0.9 (=1 × 0.9) | 16 | Filter | <4 | >99.9992 |
|  |  |  | No Filter | $5.2 \cdot 10^5$ |  |
| AF11 | 1.3 (=1 × 1.3) | 37 | Filter | 4 | 99.994 |
|  |  |  | No Filter | $6.7 \cdot 10^4$ |  |
| Donald-son HEPA | 0.4 (=1 × 0.4) | 6 | Filter | 40 | 99.992 |
|  |  |  | No Filter | $5 \cdot 10^5$ |  |

*Data from Table 1

Each AF sample has a pore size that is substantially larger than the pore size of the conventional HEPA air filter. As is generally known in filtration, larger pore size media have less propensity for clogging. This tolerance for clogging would also extend to the ability of the inventive filters to be less resistant to flooding by water droplets.

The demonstrated ability of nano alumina fibers to remove higher levels of bacteria was a surprising result and is a major benefit, particularly where the filter is used for collective protection as in a hospital where immuno-compromised patients are treated, or for protection during a biological warfare attack. Such media would also be beneficial in an improved respiratory filter to improve bacterial retention. A further benefit is the lower pressure drop of the invention as compared to HEPA, particularly as the filter loads. Finally, another advantage is that the pore size of the nano alumina filter media is much larger, resulting in a much more porous filter, allowing it to retain much more water should it be exposed to continuous loading by water droplets or mists.

Example 10

Two experiments were performed as described in Example 9, with the exception that the aerosol contained MS2 virus (25 nm size), and the testing was done at two different relative humidities. In this case the samples tested had a small pore size (~2 μm) and were 0.4 mm thick.

TABLE 7

Percentage efficiency of nano alumina filter against aerosolized MS2 virus

| Relative Humidity % | Challenge concentration, PFU/ml[a] | Filter/ No filter | Number of MS2 viruses determined in AGI-30 buffer solution, PFU | Detection limit, PFU/ml | MS2 collection efficiency by impinger % | MS2 retention efficiency % |
|---|---|---|---|---|---|---|
| 94 | 2.6 10[7] | Filter[b] | <150 | 100 | NA | >99.96 |
|  |  | No Filter[c] | 4.2 10[5] | 100 | 2.1 |  |
| 60 | 1.3 10[7] | Filter[d] | <1 | 1 | NA | >99.999 |
|  |  | No Filter[e] | 1.1 10[5] | 100 | 1.3 |  |

Notes:
[a] 2 ml of MS2 challenge solution was aerosolized;
[b] Challenge time - 6 minutes; collected volume of virus solution - 1.5 ml;
[c] Challenge time - 10 minutes; collected volume of virus solution - 2.2 ml;
[d] Challenge time - 6 minutes; collected volume of virus solution - 1.0 ml;
[e] Challenge time - 6 minutes; collected volume of virus solution - 1.5 ml.

Table 7 shows that the filter had a high collection efficiency for aerosolized virus. These results are important because viruses, which are generally one or two orders of magnitude smaller than bacteria, are very difficult to retain by depth filter media. The retention of virus by HEPA is also problematic because many pathogenic viruses are smaller than 0.1 μm in size, which is substantially smaller than the 0.3 μm test particle used in defining HEPA. Effective filtration of a monodisperse virus would be very inefficient. If the virus is enveloped in a water aerosol, then HEPA filters that are generally hydrophobic lose efficiency as water accumulates. The claimed nano alumina filter media provides a higher efficiency and capacity and would therefore be useful in filter masks and collective protection systems, such as in hospitals and for biodefense.

Calculations

From the data shown in Table 1, the air permeability $B(m^2)$ for the samples were determined as:

$$B = v\mu z/\Delta P, \quad [2]$$

where:
v—flow velocity, m/s at a given ΔP
μ—air viscocity. For air—$\mu = 18.6 \cdot 10^{-6}$ Pa s
z—thickness of the media
ΔP—pressure drop across the media, Pa Equation 2 assumes that the flow through the filter is in the viscous range. Moreover, in the case of gas-flow measurements it requires two additional conditions [2]: (i) the pore diameters are larger than 1 micron (ii) the absolute pressure on the upstream face is no greater than 1.1 times of that on the downstream face, i.e., the upstream gage pressure should be no more than 40 inches of $H_2O$, when the downstream gage pressure is zero (i.e., 400 inches of $H_2O$ absolute). When those two conditions are met Equation 2 may be used to deduce permeability.

From Eq. [2] and FIG. 1 the permeability of filter media was determined. From the permeability value and porosity the flow-averaged flow diameter, d, was determined as:

$$d^2 = 32B/\epsilon^2 \quad [3]$$

where ε—porosity.

Flow diameters d are shown in Table 1. The average pore size of the nano alumina media ranged from 4.2 to 38 μm.

From FIG. 1 as well as similar graphs for the other samples, the dependence of linear velocity of air through the media versus the applied pressure drop was determined and is shown in Table 1. From these equations the air ΔP (in mm water, gauge) at a linear flow of 3.2 m/min are compared with that of the HEPA.

While the foregoing has been set forth in considerable detail, it is to be understood that the examples and detailed embodiments are presented for elucidation and not limitation. Design variations, especially in matters of shape, size, and arrangements, may be made but are within the principles of the invention. Those skilled in the art will realize that such changes or modifications of the invention or combinations of elements, variations, equivalents, or improvements therein are still within the scope of the invention as defined in the appended claims and that the present invention may be suitably practiced in the absence of any limitation not explicitly described in this document.

We claim:

1. A filter for gaseous media, said filter comprising:
   (a) nano alumina fibers; and
   (b) second fibers mixed with said nano alumina fibers, said second fibers arranged to define a plurality of asymmetrical pores, said pores having an average pore size that is greater than about 10 μm and capable of retaining particles having a dimension that is at least one order of magnitude smaller than said average pore size.

2. A filter as in claim 1 wherein said second fibers are comprised of fibers having a smallest dimension that is larger than a minor dimension of said nano alumina fibers by about one order of magnitude.

3. A filter as in claim 1 wherein said second fibers are comprised of a combination of coarse and fine fibers.

4. A filter as in claim 3 wherein said fine fibers are comprised of more than one size of fibers.

5. A filter as in claim 1 wherein said filter is capable of removing greater than 99.97% of 0.3 μm particles from a humid air or gas stream.

6. A filter as in claim 1 wherein said filter media is capable of removing greater than 99.995% of a plurality of penetrating particles from a liquid or water aerosol.

7. A filter as in claim 1 wherein said second fibers each have a diameter that ranges from about 0.6 μm to about 3.5 μm.

8. A filter as in claim 1 wherein said asymmetrical pores have an average pore size that is greater than about 5 μm.

9. A filter as in claim 1 wherein said asymmetrical pores have an average pore size that is greater than about 10 μm.

10. A filter as in claim 1 wherein said asymmetrical pores have an average pore size that is greater than about 20 μm.

11. A filter as in claim 1 wherein said asymmetrical pores have an average pore size that is greater than about 30 μm.

12. A filter as in claim 1 wherein said nano alumina fibers have an aspect ratio that is greater than about 5 and a smallest dimension that is less than about 50 nm.

13. A filter as in claim 1 wherein said second fiber is comprised of microglass, cellulose, or fibrillated cellulose.

14. A filter as in claim 3 wherein said coarse fiber is selected from the group consisting of microglass, cellulose, or fibrillated cellulose and said fine fiber is selected from the group consisting of microglass, polymer fiber, cellulose, and fibrillated cellulose.

15. A filter as in claim 1 further comprising a granular solid.

16. A filter as in claim 15 wherein said granular solid is selected from the group consisting of fumed silica, activated carbon, and colloidal iron oxide.

17. A filter as in claim 1 further comprising a binder.

18. A filter as in claim 1 further comprising an antimicrobial agent.

19. A filter as in claim 18 wherein said antimicrobial agent is selected from the group consisting of silver, copper, zinc, and a combination thereof.

20. A filter as in claim 1 wherein said media is preconditioned with a plurality of particles.

21. A filter as in claim 20 wherein said particles have a dimension that is less than about 1.5 μm.

22. A filter as in claim 1 wherein said filter comprises more than one layer.

23. A filter as in claim 1 wherein said filter is stacked.

24. A filter as in claim 1 wherein said filter is pleated.

25. A filter as in claim 1 wherein said filter is combined with a filtration system for filtration of said gaseous medium.

26. A filter as in claim 1 wherein said gaseous medium includes a suspension of water droplets.

27. A filter as in claim 1 wherein said filter is combined with a filter that is capable of removing greater than 99.97% of 0.3 μm particles from said gaseous medium.

28. A filter as in claim 1 wherein said filter is capable of removing greater than 99.97% of 0.3 μm particles from said gaseous medium.

29. A filter as in claim 1 wherein said filter is capable of removing greater than 99.995% of a plurality of penetrating particles.

30. A method of manufacturing a filter, said method comprising the steps of:
   a. forming nano alumina fibers; and
   b. mixing second fibers with said nano alumina fibers in the presence of said second fibers to define a plurality of asymmetrical pores, said pores having an average pore size that is greater than about 10 μm and capable of retaining particles having a diameter that is at least one order of magnitude smaller than said average pore size.

31. A method as in claim 30, wherein said second fibers comprise a combination of coarse and fine fibers.

32. A method as in claim 31 wherein said fine fibers have a diameter ranging from about 0.2 μm to 2.5 μm.

33. A method as in claim 30, further comprising the step of forming said filter into a homogenous single layer.

34. A method as in claim 30, further comprising the step of pleating said filter.

35. A method as in claim 30 wherein said filter was produced by reacting aluminum powder with glass fibers in water up to about 100° C.

36. A method of filtering a gaseous medium, said method comprising the steps of:
   a. passing a gaseous medium through a filter comprising a plurality of nano alumina fibers mixed with a plurality of second fibers to define a plurality of asymmetrical pores, said pores having an average pore size that is greater than about 10 μm; and
   b. retaining a plurality of particles from said gaseous medium, said particles having dimension that is about an order of magnitude smaller than said average pore size.

37. A method of filtering as in claim 36 wherein said filter is used in a room air filtration system.

38. A method of filtering as in claim 36 wherein said filter is used to remove paint particles from an air or gas stream.

39. A method of filtering as in claim 36 wherein said filter is used in a respirator.

40. A method of filtering as in claim 36 wherein said filter is used in an automotive air filter.

41. A method of filtering as in claim 37 wherein said room is a clean room.

42. A method of filtering as in claim 37 wherein said room is an operating room.

43. A method of filtering as in claim 37 wherein said room houses at least one immune-comprised patient.

44. A method of manufacturing a filter, said method comprising the steps of:
   a. forming nano alumina fibers; and
   b. arranging a plurality of second fibers in a matrix with said nano alumina fibers to create a plurality of asymmetric pores into which said nano alumina fibers are dispersed, said pores each having an average pore size that greater than about 10 μm.

* * * * *